(12) United States Patent
Zannis et al.

(10) Patent No.: US 7,819,880 B2
(45) Date of Patent: Oct. 26, 2010

(54) IMPLANT DELIVERY INSTRUMENT

(75) Inventors: Anthony D. Zannis, Ft Wayne, IN (US);
Thomas S. Camino, Warsaw, IN (US);
John W. Kemppainen, Richland, MI
(US); Herbert E. Schwartz, Ft Wayne,
IN (US); Danny E. McAdams, Warsaw,
IN (US)

(73) Assignee: Depuy Products, Inc., Warsaw, IN (US)

( * ) Notice: Subject to any disclaimer, the term of this patent is extended or adjusted under 35 U.S.C. 154(b) by 1011 days.

(21) Appl. No.: 10/610,288

(22) Filed: Jun. 30, 2003

(65) Prior Publication Data

US 2004/0267277 A1     Dec. 30, 2004

(51) Int. Cl.
*A61F 2/00* (2006.01)

(52) U.S. Cl. .................. 606/99; 606/86 A; 606/914

(58) Field of Classification Search .......... 606/232, 606/99, 142, 139, 108, 219, 220, 86 R, 86 A, 606/914; 604/60
See application file for complete search history.

(56) References Cited

U.S. PATENT DOCUMENTS

| | | | | |
|---|---|---|---|---|
| 2,008,380 | A | * | 7/1935 | Bachmann .................. 128/838 |
| 3,921,632 | A | * | 11/1975 | Bardani .................... 604/891.1 |
| 4,122,556 | A | | 10/1978 | Poler |
| 4,349,027 | A | | 9/1982 | DiFrancesco |
| 4,681,102 | A | * | 7/1987 | Bartell .......................... 606/1 |
| 4,741,330 | A | * | 5/1988 | Hayhurst .................... 606/144 |
| 4,750,498 | A | | 6/1988 | Graham |
| 4,836,202 | A | | 6/1989 | Krasner |
| 4,873,976 | A | | 10/1989 | Schreiber |
| 4,880,429 | A | | 11/1989 | Stone |
| 4,981,841 | A | | 1/1991 | Gibson |
| 5,007,934 | A | | 4/1991 | Stone |
| 5,036,733 | A | | 8/1991 | Tiholiz et al. |
| 5,108,421 | A | | 4/1992 | Fowler |
| 5,108,438 | A | | 4/1992 | Stone |
| 5,129,882 | A | | 7/1992 | Weldon |
| 5,141,507 | A | | 8/1992 | Parekh |
| 5,190,552 | A | | 3/1993 | Kelman |
| 5,290,310 | A | | 3/1994 | Makower |
| 5,306,311 | A | | 4/1994 | Stone |

(Continued)

OTHER PUBLICATIONS

O'Connor's Textbook of Arthroscopic Surgery, 2$^{nd}$ ed., 1992, Chapter 19.

(Continued)

*Primary Examiner*—Thomas C Barrett
*Assistant Examiner*—James L Swiger

(57) ABSTRACT

A surgical instrument has an elongate guide member and a reciprocable member. The elongate guide member provides a protected path of travel for an implant from outside the body to a position near a damaged tissue site. The reciprocable member is movable along the elongate guide member to push the implant along its path of travel. The reciprocable member can include an implant carrier. The implant can be an orthopaedic implant for repair or regeneration of soft tissue at a damaged joint site. The implant can be larger than the transverse dimension of the elongate guide member and folded or rolled to fit within the elongate guide member. Use of this instrument protects the implant from damage as it is delivered to the damaged joint site. The invention also includes a surgical method for delivering an implant to a damaged tissue site.

31 Claims, 15 Drawing Sheets

U.S. PATENT DOCUMENTS

| | | | |
|---|---|---|---|
| 5,320,633 A | 6/1994 | Allen | |
| 5,320,639 A | 6/1994 | Rudnick | |
| 5,374,268 A | 12/1994 | Sander | |
| 5,569,252 A | 10/1996 | Justin | |
| 5,571,109 A | 11/1996 | Bertagnoli | |
| 5,653,715 A | 8/1997 | Reich et al. | |
| 5,681,353 A | 10/1997 | Li | |
| 5,702,418 A | 12/1997 | Ravenscroft | |
| 5,702,462 A | 12/1997 | Oberlander | |
| 5,735,903 A | 4/1998 | Li | |
| 5,782,830 A * | 7/1998 | Farris | 606/99 |
| 5,873,906 A | 2/1999 | Lau | |
| 5,919,225 A | 7/1999 | Lau | |
| 5,951,587 A | 9/1999 | Qureshi | |
| 5,968,052 A | 10/1999 | Sullivan | |
| 5,971,987 A | 10/1999 | Huxel et al. | |
| 5,980,524 A | 11/1999 | Justin | |
| 5,984,926 A | 11/1999 | Jones | |
| 5,993,475 A | 11/1999 | Lin | |
| 6,015,429 A | 1/2000 | Lau | |
| 6,042,582 A | 3/2000 | Ray | |
| 6,042,610 A | 3/2000 | Li | |
| 6,056,778 A | 5/2000 | Grafton | |
| 6,146,385 A | 11/2000 | Torrie et al. | |
| 6,152,935 A | 11/2000 | Kammerer | |
| 6,156,044 A | 12/2000 | Kammerer | |
| 6,176,880 B1 | 1/2001 | Plouhar | |
| 6,238,402 B1 | 5/2001 | Sullivan | |
| 6,273,893 B1 | 8/2001 | McAllen et al. | |
| 6,280,449 B1 | 8/2001 | Blake | |
| 6,293,961 B2 | 9/2001 | Schwartz | |
| 6,306,156 B1 | 10/2001 | Clark | |
| 6,306,159 B1 | 10/2001 | Schwartz | |
| 6,319,258 B1 | 11/2001 | McAllen et al. | |
| 6,319,271 B1 | 11/2001 | Schwartz | |
| 6,350,274 B1 | 2/2002 | Li | |
| 6,391,051 B2 | 5/2002 | Sullivan | |
| 6,432,123 B2 | 8/2002 | Schwartz et al. | |
| 6,491,697 B1 | 12/2002 | Clark et al. | |
| 6,572,626 B1 * | 6/2003 | Knodel et al. | 606/139 |
| 6,605,093 B1 | 8/2003 | Blake | |
| 6,652,561 B1 * | 11/2003 | Tran | 606/232 |
| 6,770,078 B2 | 8/2004 | Bonutti | |
| 6,929,606 B2 | 8/2005 | Ritland | |
| 7,160,326 B2 | 1/2007 | Ball | |
| 7,468,041 B2 | 12/2008 | Rhodes et al. | |
| 7,473,259 B2 | 1/2009 | Jacobs et al. | |
| 7,559,941 B2 | 7/2009 | Zannis et al. | |
| 7,563,266 B2 | 7/2009 | Camino et al. | |
| 2001/0023352 A1 | 9/2001 | Gordon | |
| 2004/0260305 A1 * | 12/2004 | Gorensek et al. | 606/99 |
| 2004/0267277 A1 | 12/2004 | Zannis et al. | |
| 2006/0095048 A1 | 5/2006 | Zannis et al. | |
| 2006/0095049 A1 | 5/2006 | Zannis et al. | |
| 2006/0095053 A1 | 5/2006 | Zannis et al. | |
| 2006/0095054 A1 | 5/2006 | Zannis et al. | |
| 2006/0211953 A1 | 9/2006 | Zannis et al. | |

OTHER PUBLICATIONS

Rodeo, "Arthroscopic Meniscal Repair With Use of Outside-In Technique", Instr. Course Lect., 2000, 49, pp. 195-206.

\* cited by examiner

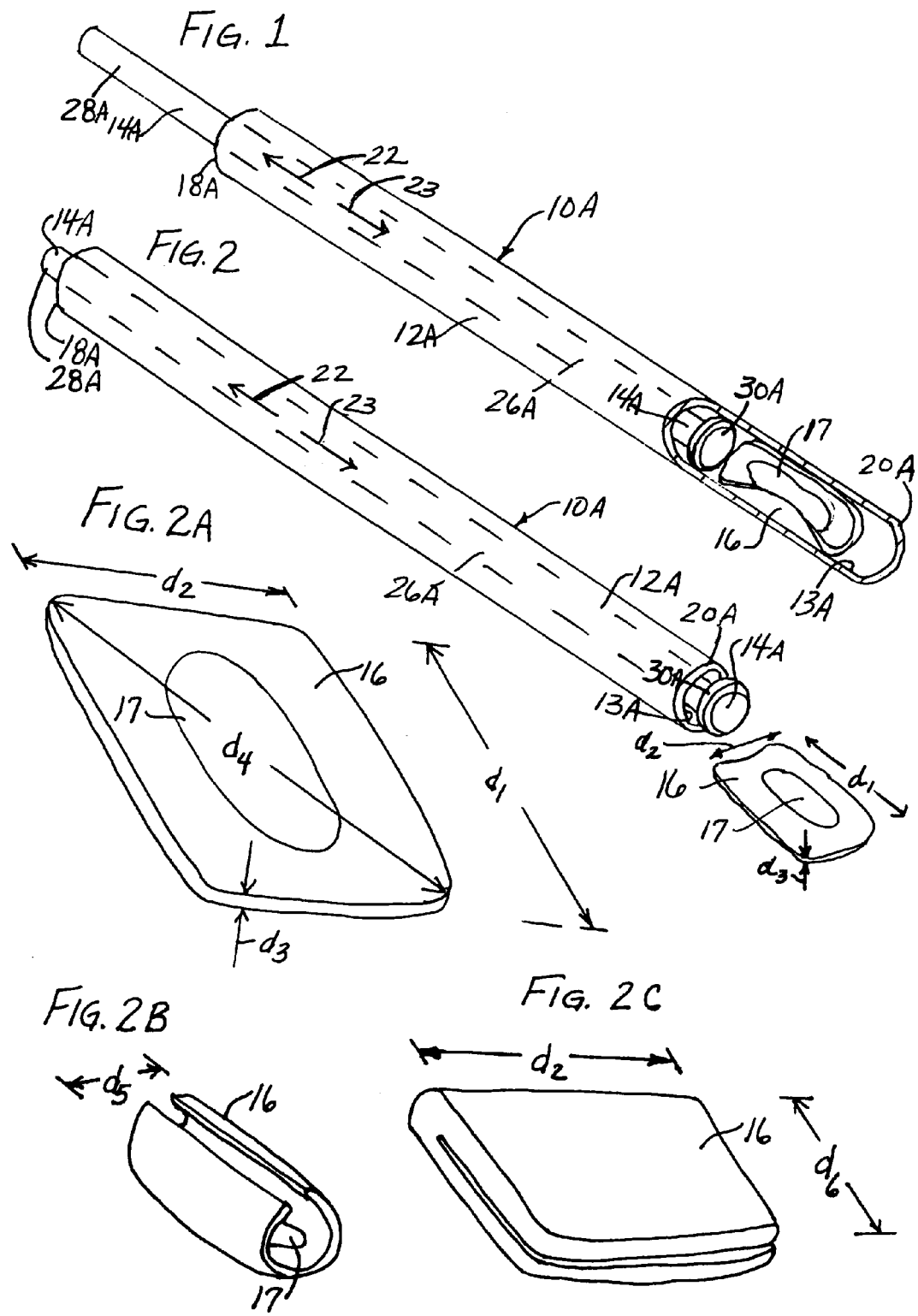

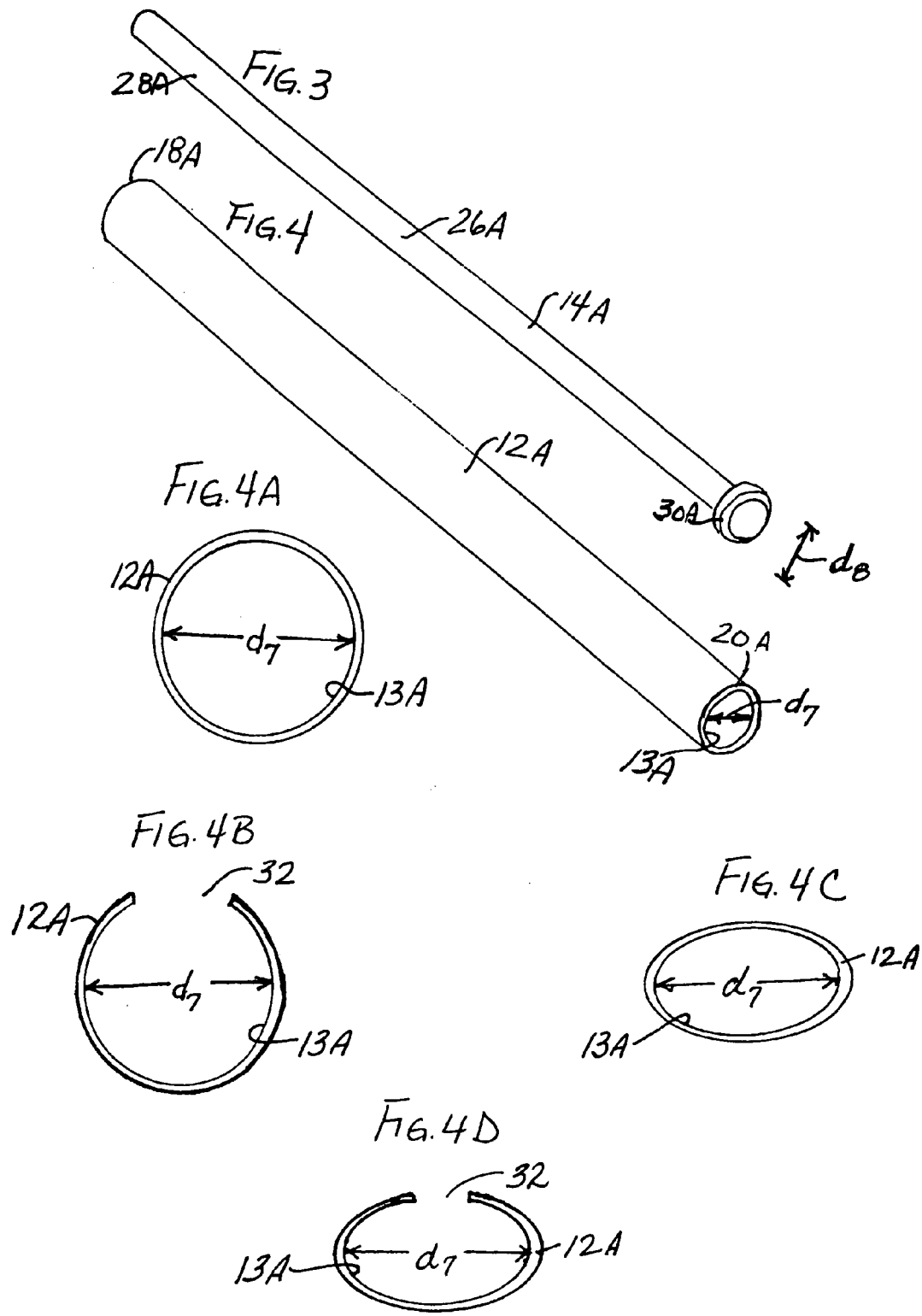

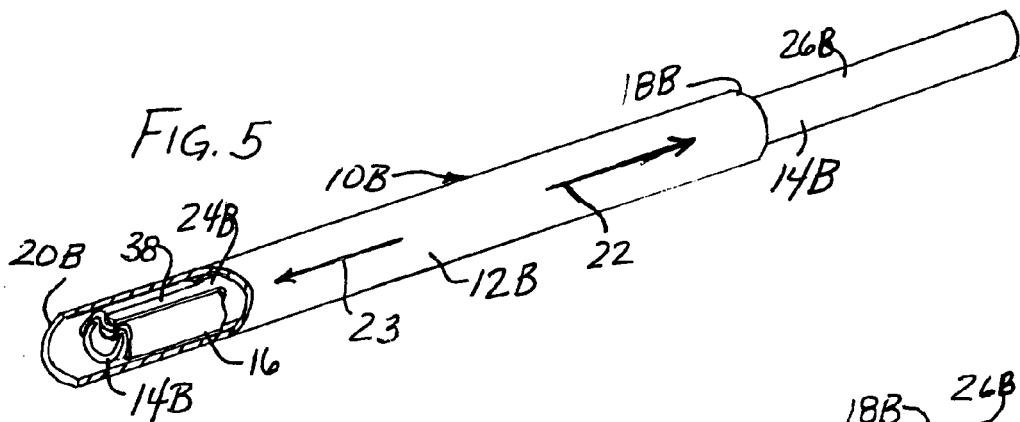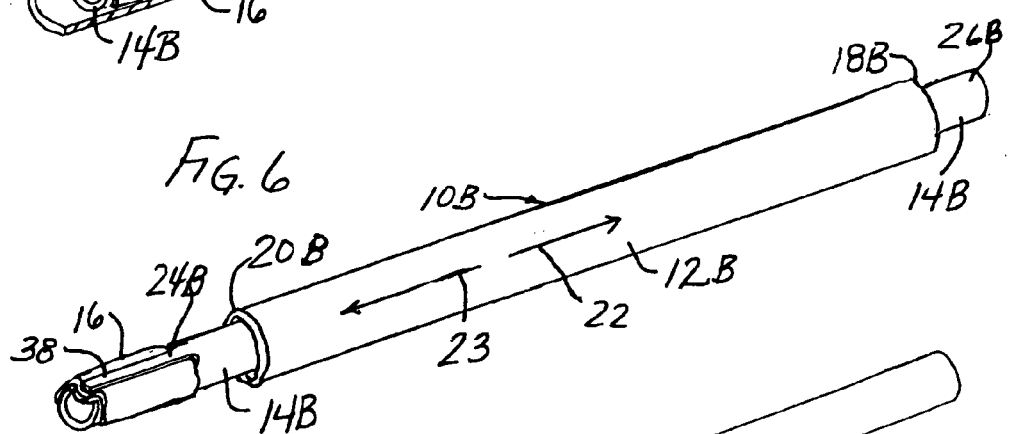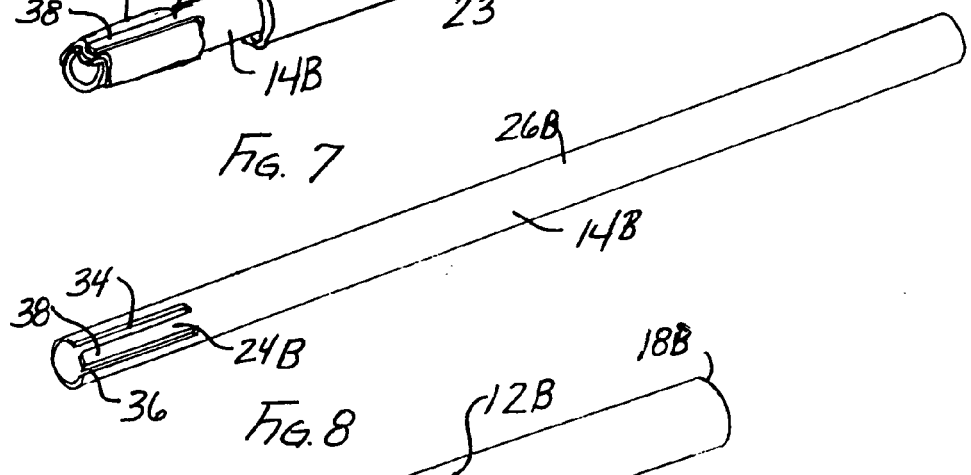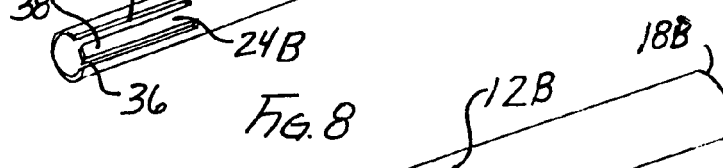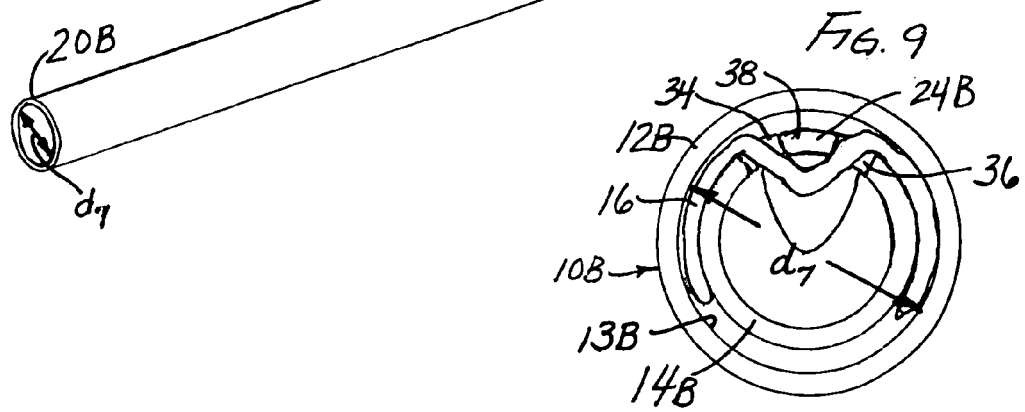

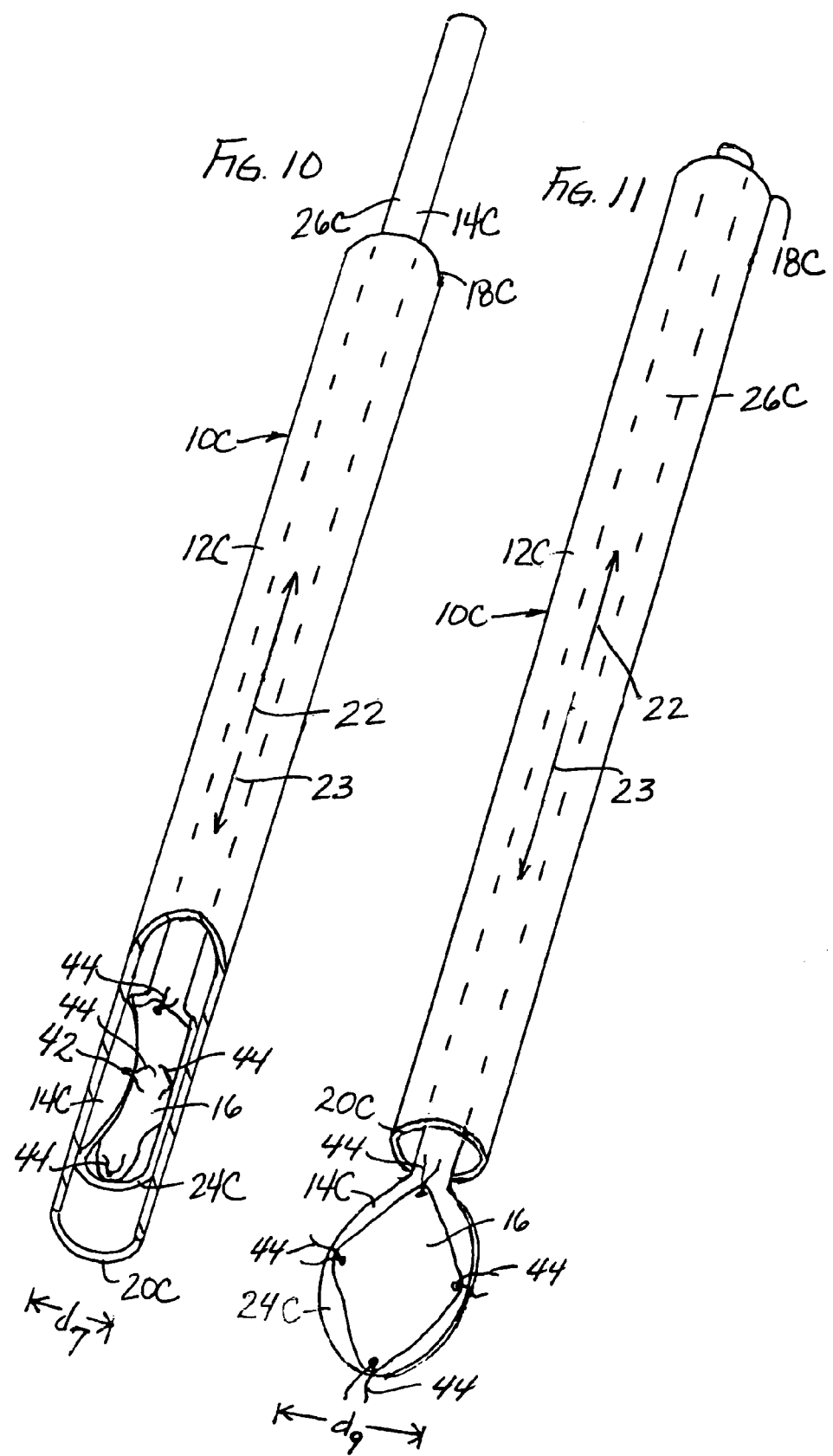

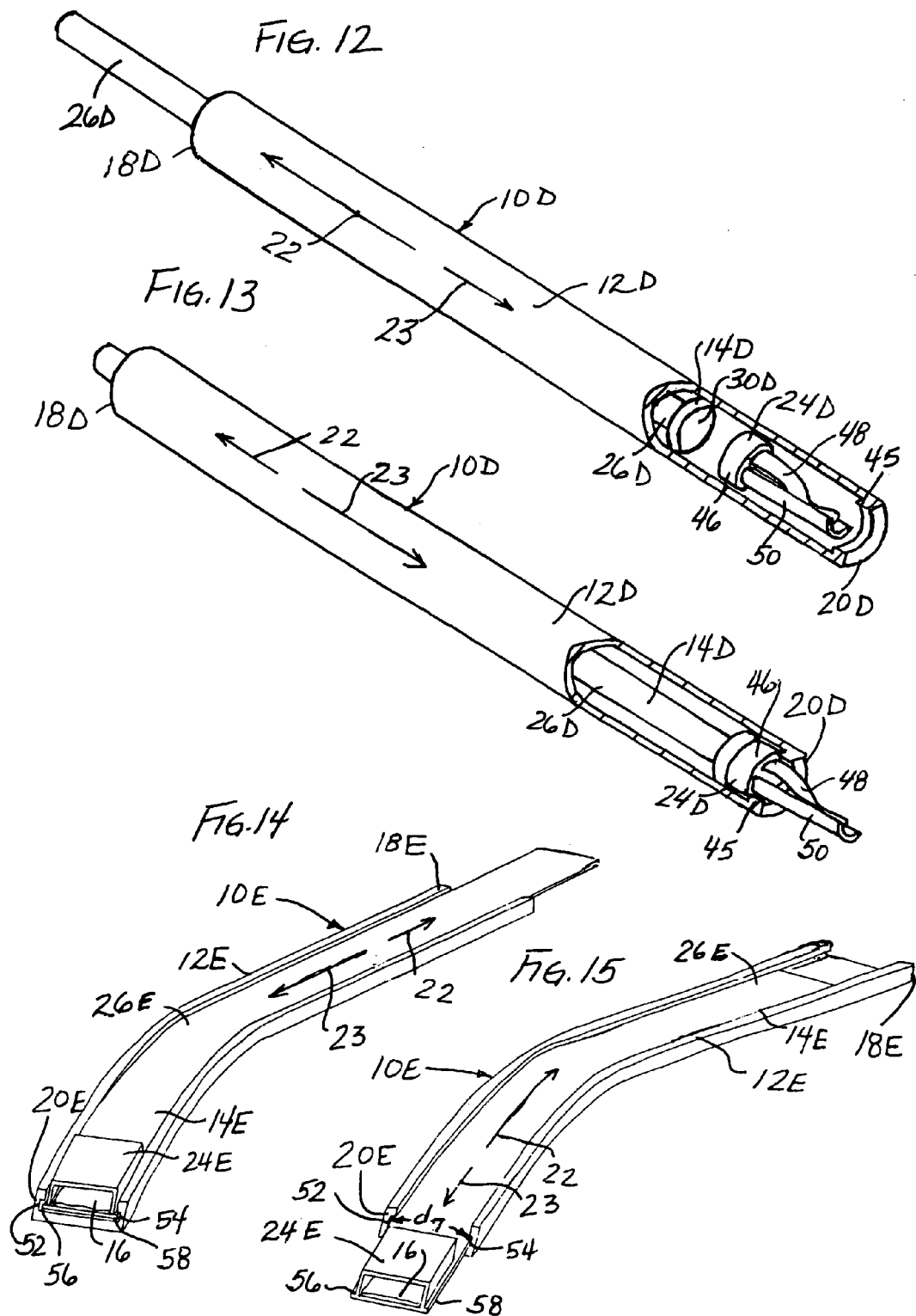

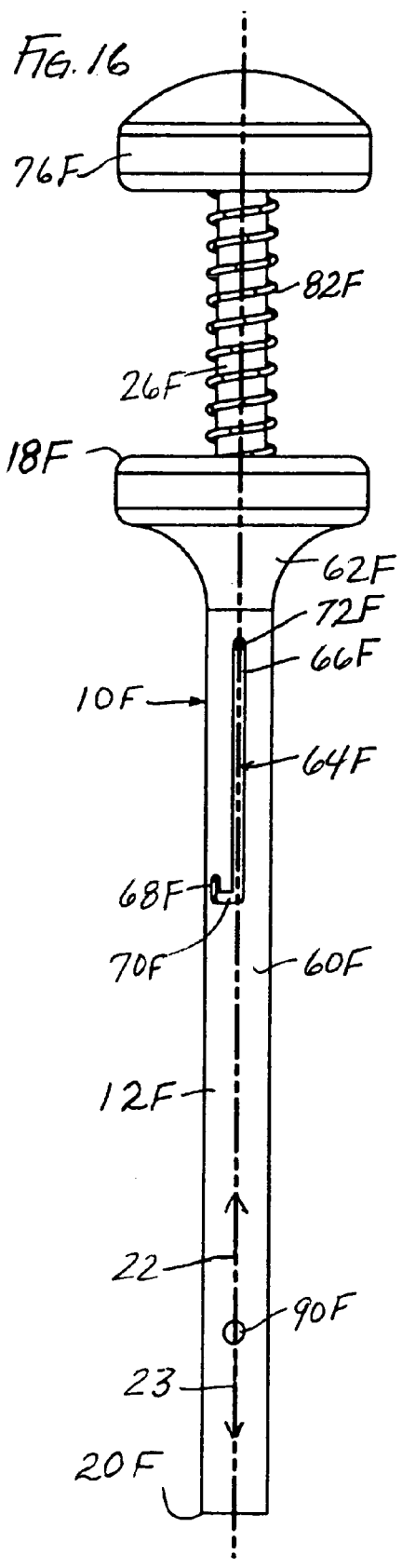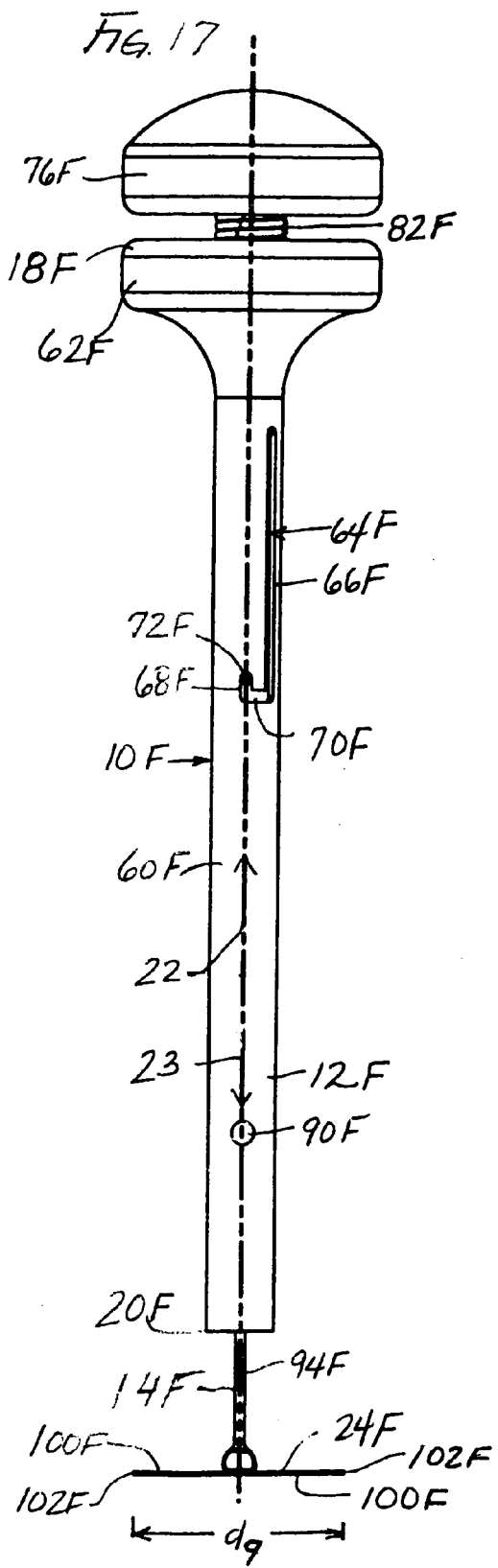

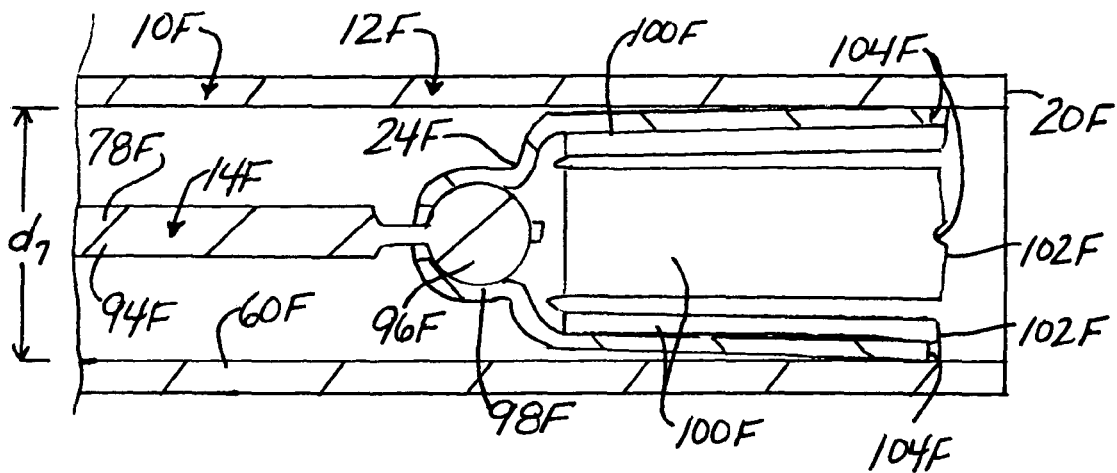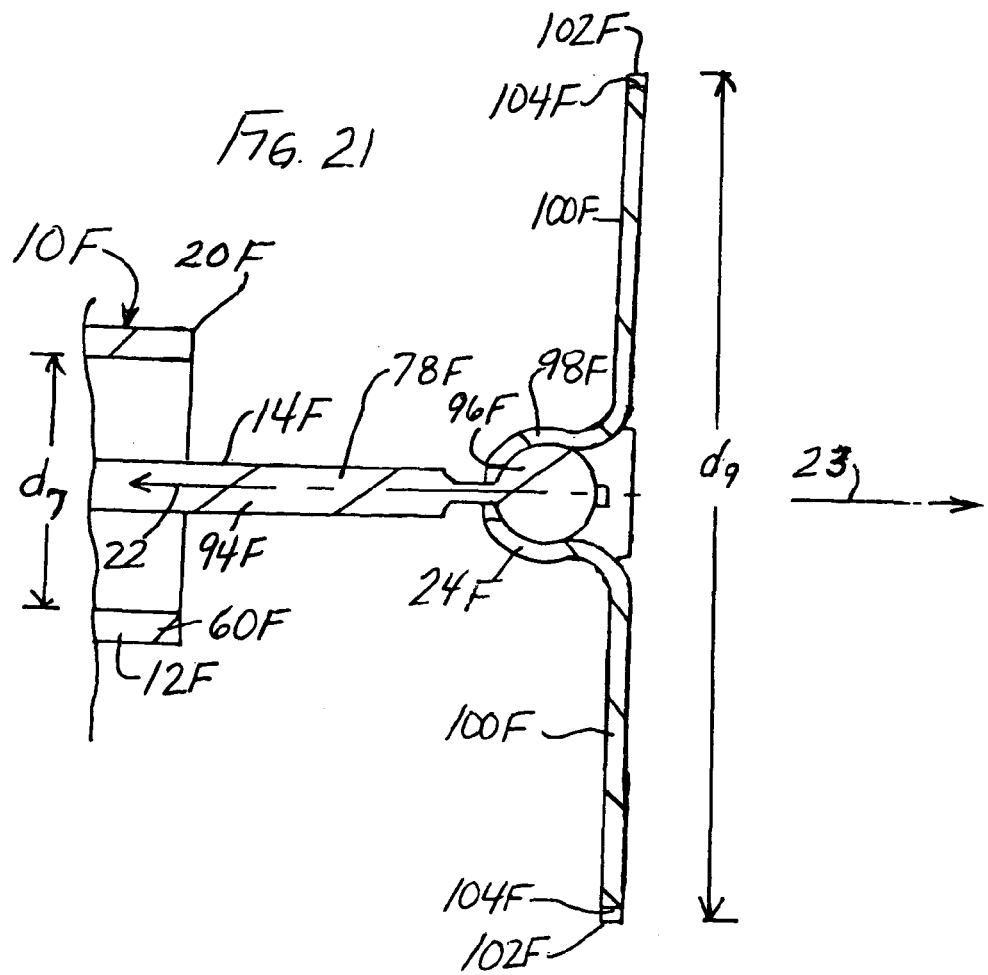

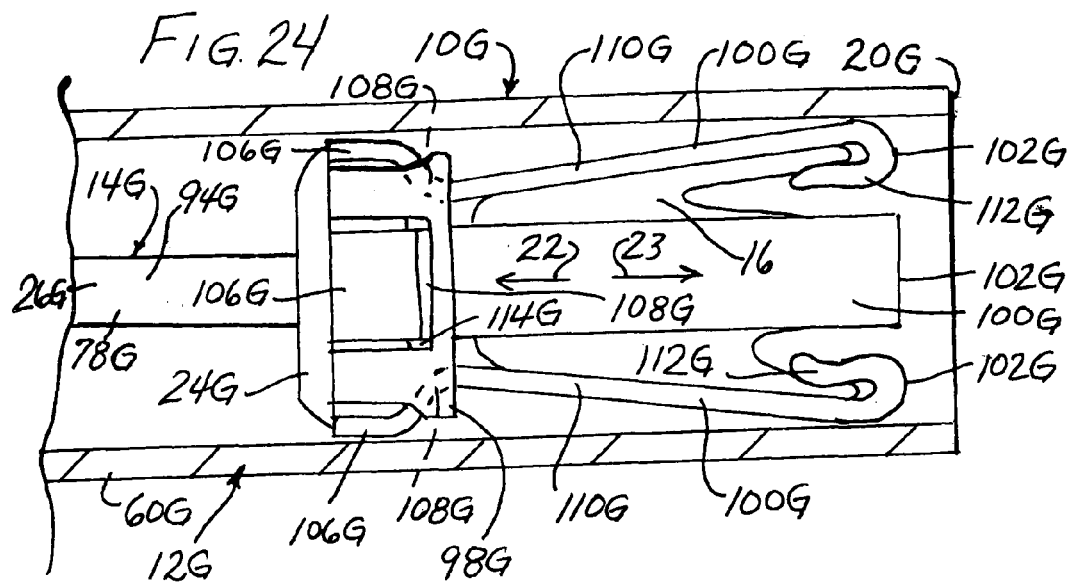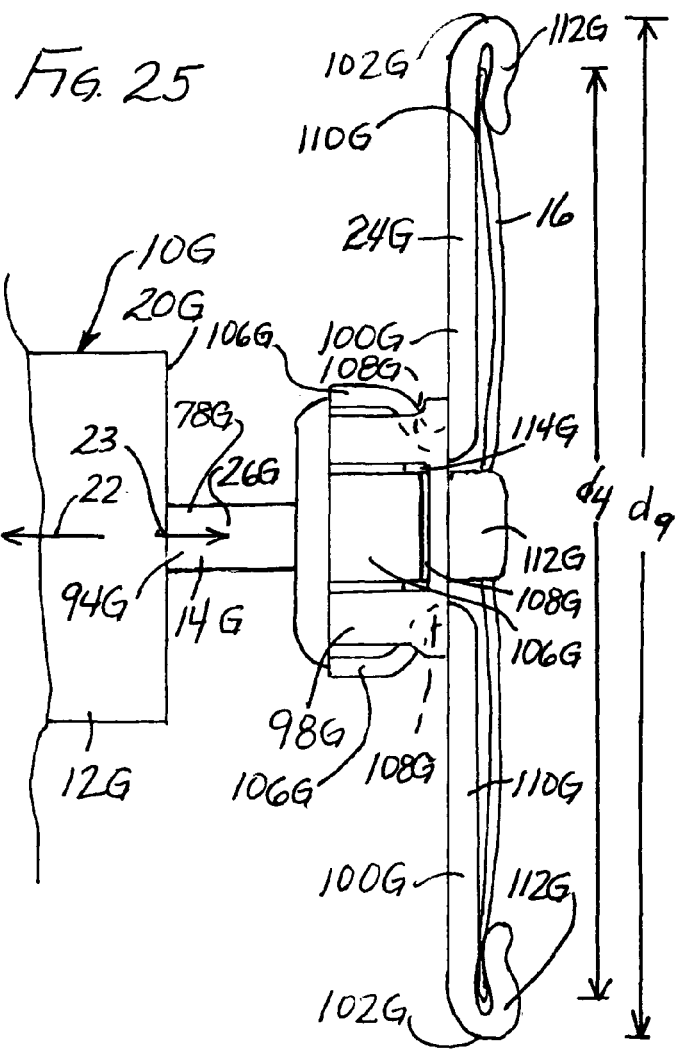

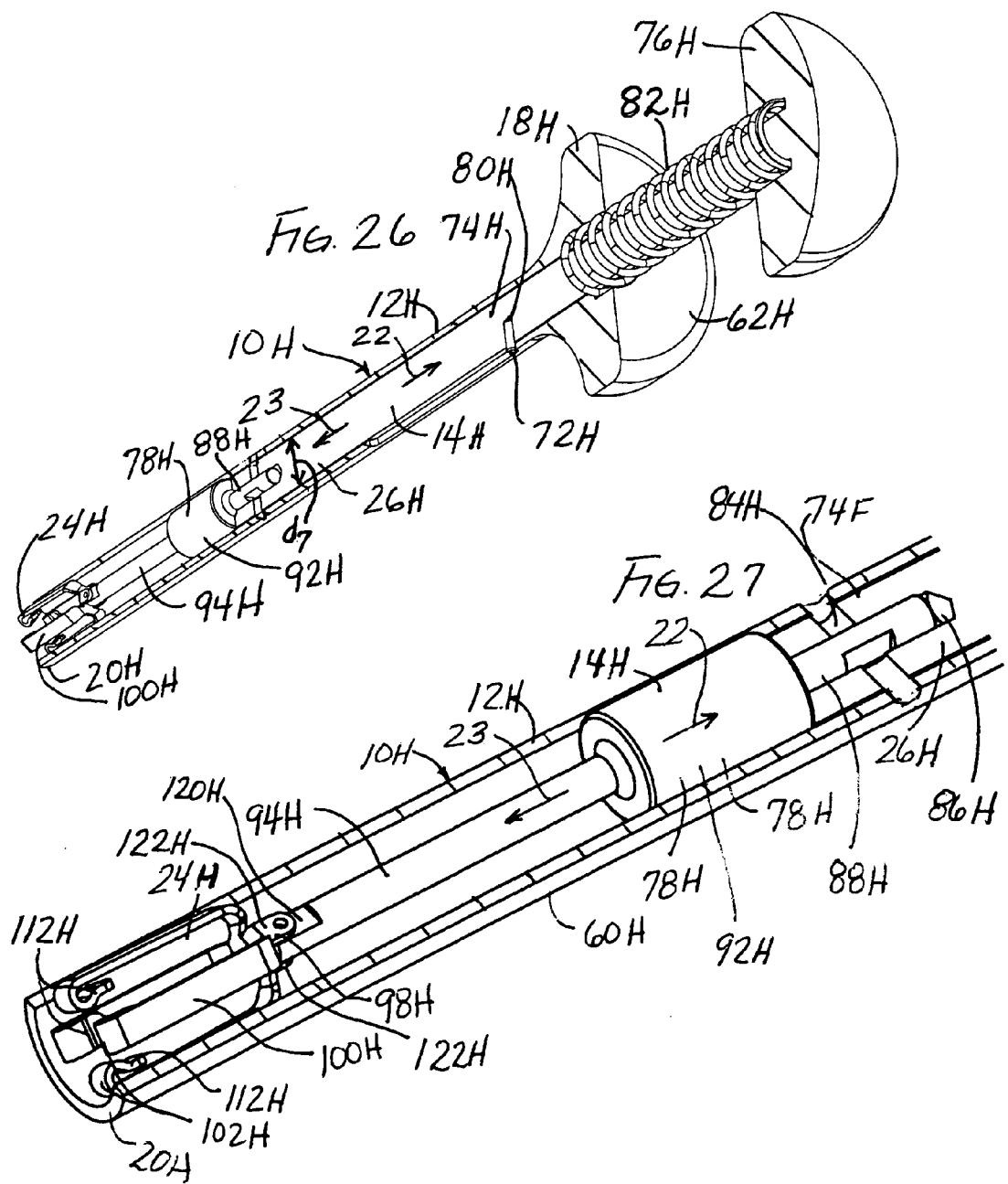

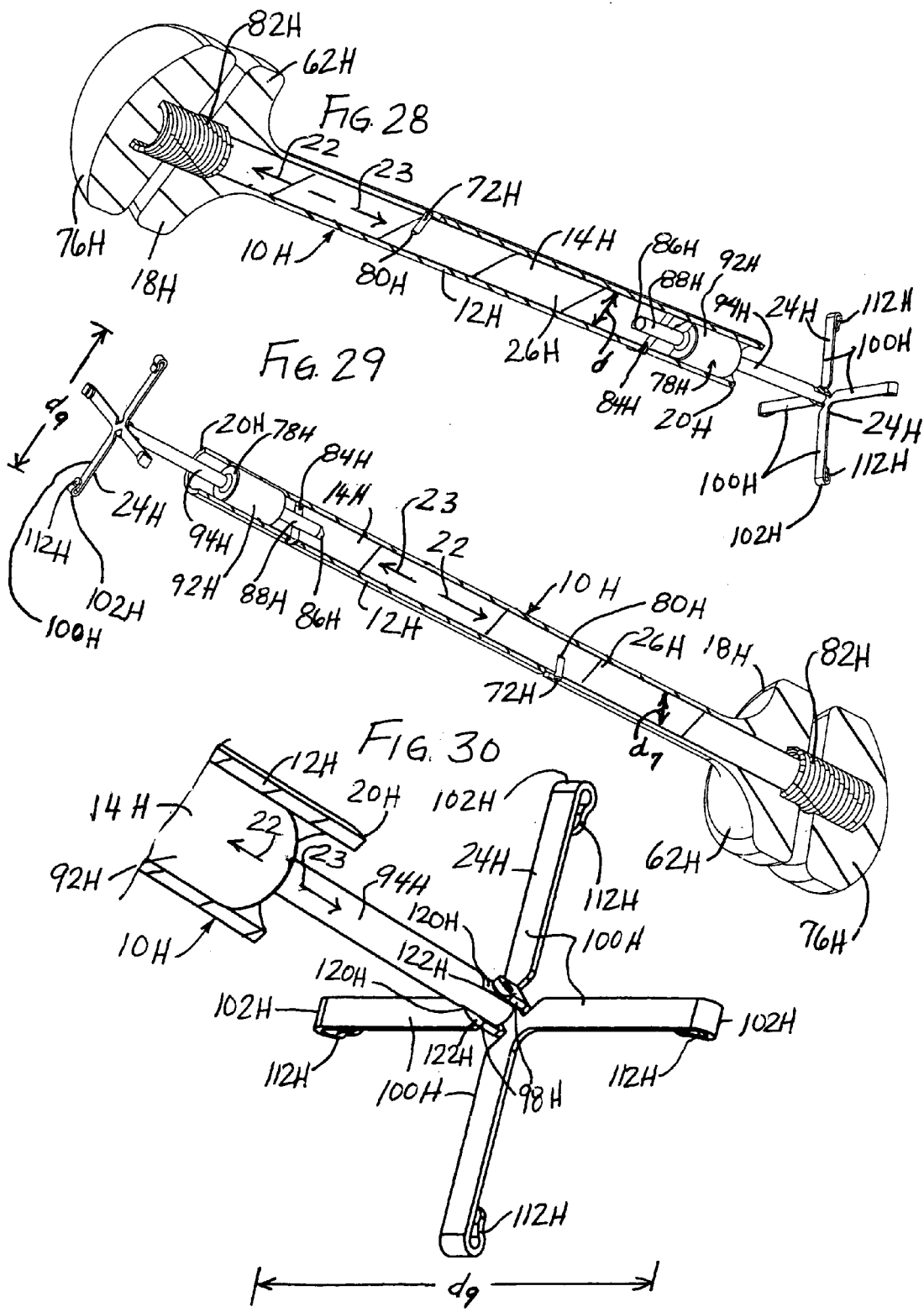

IMPLANT DELIVERY INSTRUMENT

FIELD OF THE INVENTION

The present invention relates generally to a surgical instrument for delivering an implant to a damaged tissue site in the human body.

BACKGROUND OF THE INVENTION

Several different types of soft tissue are found in human joints. For example, a joint can include articular hyaline cartilage, intra-articular fibrocartilage, tendons and ligaments. Articular hyaline cartilage is found on the surfaces of the bones of the joint. Intra-articular cartilage is found between the joint surfaces. Tendons connect muscle to the bones of the joint, and ligaments connect articular extremities of the bones of the joint.

When the soft tissue of a joint is no longer healthy, there can be debilitating pain in the joint. Soft tissue health can be adversely affected by disease, aging, or trauma. The adverse effects of disease, aging and trauma can be, for example, in the form of a tear in the soft tissue, or in the form of a breakdown, thinning or delamination of the tissue.

One form of intra-articular cartilage that is frequently damaged or degenerated is the meniscus of the knee. The meniscus is frequently damaged in twisting injuries. It is also damaged with repetitive impact over time. Meniscus degeneration can also occur by aging; as a person ages, the meniscus can become soft in places, so that even common motions like squatting can cause meniscal tears.

Common surgical procedures for treating meniscal damage include tear repairs and menisectomies. A tear repair is most commonly performed when the tear is a clean longitudinal vertical lesion in the vascular red zone of the meniscus. The basic strategy is to stabilize the tear by limiting or eliminating radial separation of the faces of the tear when the meniscus is load bearing. Many devices and surgical procedures exist for repairing meniscal tears by approximating the faces of the meniscus at the tear. Examples of such devices and procedures are disclosed in the following U.S. Pat. Nos. 6,319,271; 6,306,159; 6,306,156; 6,293,961; 6,156,044; 6,152,935; 6,056,778; 5,993,475; 5,980,524; 5,702,462; 5,569,252; 5,374,268; 5,320,633; and 4,873,976.

Menisectomies involve the surgical removal of part of the meniscus. Such procedures have generally been performed in cases of radial tears, horizontal tears, vertical longitudinal tears outside the vascular zone, complex tears, or defibrillation. Although menisectomies provide immediate relief to the patient, in the long term the absence of part of the meniscus can cause cartilage wear on the condylar surface, eventually leading to arthritic conditions in the joint.

Such surgical procedures are commonly performed arthroscopically. In arthroscopy, small incisions are made at the affected joint to form portals for the insertion of instruments, including a small lens and lighting system (an arthroscope). The arthroscope is connected to a viewing device, such as a television monitor to allow the surgeon to see the interior of the joint. Other instruments are inserted through other portals to perform a variety of tasks. For example, the surgical instrument may include an implement for manipulating native tissue (for example, tissue grasping, tissue cutting, bone abrading).

Typical surgical instruments used in arthroscopic procedures include rongeurs, such as the Kerrison rongeur, punch forceps, basket forceps, suction punches and cup curet, for example. Examples of arthroscopic instruments are described and illustrated in O'Connor's Textbook of Arthroscopic Surgery, $2^{nd}$ ed., 1992, Chapter 19.

Other common surgical techniques in orthopaedic surgery include open surgery and mini-arthrotomy. For example, for knee surgery, the surgery may be performed by an open knee arthrotomy, where the incision may typically be 20-30 cm in length, and wherein the patella is everted during surgery. Knee surgery may also be performed by a mini-knee arthrotomy, where the incision is typically 10-13 cm in length and patella tension is avoided.

Intra-articular fibrocartilage is also present, for example, in the temporomandibular joint and between vertebrae. Injury and degeneration can also occur to the intra-articular fibrocartilage in these other joints.

Another common site of soft tissue injury and degeneration is the rotator cuff in the shoulder. The rotator cuff comprises the tendons that attach muscles to a bone in the shoulder. Where one of the tendons is thin, delaminated or frayed to the point that surgical repair or reconstruction is necessary, the damaged tendon can be reinforced with graft tissue or with an orthopaedic implant.

A variety of orthopaedic implants are available for treating damaged soft tissue at a joint site. One commercially available orthopaedic implant is the RESTORE™ orthobiologic implant. The RESTORE™ orthobiologic implant comprises layers of small intestine submucosa. The commercial RESTORE™ product is typically sold in the form of a thin circular sheet with a diameter of about 2.5 inches in diameter. Other shapes and sizes of RESTORE™ orthobiologic implants can be used. In addition, the surgeon can cut the commercial RESTORE™ product intra-operatively to the desired shape and size. The RESTORE™ implant is used in treating rotator cuff injuries.

Orthopaedic implants for treatment of damaged menisci are disclosed in the following U.S. Pat. Nos. 6,042,610; 5,735,903; 5,681,353; 5,306,311; 5,108,438; 5,007,934; and 4,880,429.

SUMMARY OF THE INVENTION

Orthopaedic implants useful in approximating, repair or regeneration of fibrocartilage are disclosed in the following applications for U.S. patent Ser. No. 10/195,794 entitled "Meniscus Regeneration Device and Method"; Ser. No. 10/195,719 entitled "Devices from Naturally Occurring Biologically Derived Materials"; Ser. No. 10/195,347 (now U.S. Pat. No. 7,361,195 issued Apr. 22, 2008), entitled "Cartilage Repair Apparatus and Method"; Ser. No. 10/195,344 (now U.S. Pat. No. 7,163,563 issued Jan. 16, 2007), entitled "Unitary Surgical Device and Method"; Ser. No. 10/195,341 entitled "Hybrid Biologic/Synthetic Porous Extracellular Matrix Scaffolds"; Ser. No. 10/195,606 entitled "Cartilage Repair and Regeneration Device and Method"; Ser. No. 10/195,354 entitled "Porous Extracellular Matrix Scaffold and Method"; Ser. No. 10/195,334 entitled "Cartilage Repair and Regeneration Scaffolds and Method"; Ser. No. 10/195,633 (now U.S. Pat. No. 7,201,917 issued Apr. 10, 2007), entitled "Porous Delivery Scaffold and Method", each of which is assigned to the same assignee as the present application, each of which was filed on Jul. 15, 2002, and each of which is hereby incorporated by reference herein. Cross reference is also made to U.S. patent application Ser. No. 10/172,347 entitled "Hybrid Biologic-Synthetic Bioabsorbable Scaffolds" which was filed on Jun. 14, 2002, which is assigned to the same assignee as the present application, and which is incorporated by reference herein. Additional orthopaedic implants are disclosed in U.S. Pat. No. 6,176,880, entitled "Tissue Grant Construct for Replacement of Cartilaginous Structures" and U.S. patent application Ser. Nos. 09/767,345 and 09/767,346 of the same title, both filed on Jan. 23, 2001 and claiming priority to U.S. Pat. No. 6,176,880, which are incorporated by reference herein (U.S. Ser. No. 09/767,346 issued as U.S. Pat. No. 6,793,676 on Sep. 21, 2004).

As used herein "implant" is intended to mean any device that is intended to be implanted at a damaged tissue site for the approximation, repair or regeneration of tissue at the damaged tissue site. "Orthopaedic implant" is intended to mean any device that is intended to be implanted at a joint site for the approximation, repair or regeneration of soft tissue at the joint site. While "implant" and "orthopaedic implant" are intended to include all of the devices identified in the preceding paragraph and commercial devices such as the RESTORE™ orthobiologic implant, "implant" and "orthopaedic implant" should not be limited to these particular devices or to any particular material unless expressly set forth in the claims. For example, "implant" and "orthopaedic implant" as used herein are intended to include devices made from synthetic sources, from purified natural fibers as well as devices made from naturally occurring tissue. An implant may comprise a tissue scaffold, patch or graft (including autografts, allografts and hetergrafts), for example. In addition, "implant" and "orthopaedic implant" are intended to include such devices either alone or in combination with bioactive agents, biologically-derived agents, cells, a biological lubricant, a biocompatible synthetic or a biocompatible inorganic material, for example.

Materials forming orthopaedic implants can find use in other parts of the body as well. Accordingly, the term "implant" is intended to mean such materials regardless of their intended end use.

The present invention provides a surgical instrument and method that allow for delivery of implants to a damaged tissue site. The damaged tissue site can be a damaged joint site, such as in the area of the meniscus in the human knee joint or in the area of the rotator cuff of the shoulder joint, and the biologic implant can be an orthopaedic implant used to approximate, repair or regenerate damaged or diseased soft tissue at the damaged joint site.

In one aspect, the present invention provides a surgical instrument for delivering an implant to a damaged tissue site in a human body. The instrument comprises an elongate guide member and a reciprocable member. The elongate guide member has a proximal end and a distal end. The elongate guide member provides a path of travel for the implant from the proximal end to the distal end. The reciprocable member is used to move the implant from a position along the elongate guide member to a position beyond the distal end of the elongate guide member at the damaged tissue site. The instrument also includes an implant carrier for carrying the implant so that the implant can be moved along the path of travel by moving the implant carrier. The implant carrier and the reciprocable member are discrete elements connected to define an assembly. The implant carrier comprises a base and a plurality of arms extending from the base. Each arm has a free end opposite the base. The implant carrier has a retracted position between the proximal end and distal end of the elongate guide member and an extended position beyond the distal end of the elongate guide member. When the implant carrier is in the retracted position, the arms of the implant carrier have a general longitudinal orientation with the free ends of the arms positioned distally away from the base and the reciprocable member when the implant carrier is in the retracted position. When the implant carrier is in the extended position, the arms of the implant carrier have a general radial orientation with the free ends of the arms positioned radially away from the base and the reciprocable member. The implant carrier has a transverse dimension perpendicular to the path of travel of the implant. The maximum transverse dimension of the implant carrier in the retracted position is less than the maximum transverse dimension of the implant carrier in the extended position. The instrument also includes a spring for urging the implant carrier to the retracted position. At least two of the instrument members include complementary structures for temporarily locking the implant carrier in the extended position.

In another aspect, the present invention provides a tissue repair system comprising a surgical instrument and an implant, the surgical instrument for delivering the implant to a damaged tissue site in a human body. The surgical instrument comprises an implant carrier, an elongate guide member and a reciprocable pusher member. The elongate guide member has a proximal end and a distal end. The elongate guide member provides a path of travel for the implant carrier from the proximal end to the distal end of the elongate guide member. The implant carrier has an extended position beyond the distal end of the elongate guide member and a retracted position between the proximal and distal ends of the elongate guide member. The reciprocable pusher member is used to move the implant carrier between the retracted and extended positions. The implant carrier comprises a base and a plurality of arms extending outwardly from the base. Each arm has a free end opposite the base. The arms of the implant carrier have a general longitudinal orientation with the free ends of the arms positioned distally away from the base and the reciprocable member when the implant carrier is in the retracted position. The arms of the implant carrier having a general radial orientation with the free ends of the arms positioned radially away from the base and the reciprocable member when the implant carrier is in the extended position. The implant carrier has a transverse dimension perpendicular to the path of travel of the implant. The maximum transverse dimension of the implant carrier in the retracted position is less than the maximum transverse dimension of the implant carrier in the extended position. The implant includes a sheet attached to the free ends of a plurality of the arms of the implant carrier when the implant carrier is in the retracted position and when the implant carrier is in the extended position. The implant has a first shape when the implant carrier is in the retracted position and a second shape when the implant carrier is in the extended position.

In another aspect, the present invention provides a method of delivering an implant to a damaged tissue site in a body. A surgical instrument is provided. The instrument includes an elongate guide member having a proximal end and a distal end. The distal end of the elongate guide member is placed near the damaged joint site in the body. The implant is positioned between the proximal and distal end of the elongate guide member. The implant is moved along the elongate guide member until the implant is at the damaged tissue site.

BRIEF DESCRIPTION OF THE DRAWINGS

The invention will be better understood by reference to the figures of the drawings wherein like numbers denote like parts throughout and wherein:

FIG. 1 is a perspective view of a first embodiment of a surgical instrument together with an orthopaedic implant, with part of the distal end of the elongate guide member component of the surgical instrument shown in cross-section, and with an orthopaedic implant and reciprocable member component shown in a retracted position;

FIG. 2 is a perspective view of the surgical instrument of FIG. 1, with the reciprocable member component shown in an extended position and the orthopaedic implant outside the distal end of the surgical instrument;

FIG. 2A is a perspective view of an example of an orthopaedic implant;

FIG. 2B is a perspective view of the orthopaedic implant of FIG. 2A, shown rolled into a more narrow shape to fit within the surgical instrument of FIGS. 1-2;

FIG. 2C is a perspective view of the orthopaedic implant of FIG. 2A, shown folded along its transverse centerline for delivery of a smaller implant to the damaged joint site;

FIG. 3 is a perspective view of the reciprocable member component of the surgical instrument of FIGS. 1-2, shown disassembled from the elongate guide member component of the surgical instrument;

FIG. 4 is a perspective view of the elongate guide member component of the surgical instrument of FIGS. 1-2, shown disassembled from the reciprocable member component of the surgical instrument;

FIG. 4A is an end view of the elongate guide member component of FIG. 4;

FIG. 4B is an end view of an alternate elongate guide member component;

FIG. 4C is an end view of another alternate elongate guide member component;

FIG. 4D is an end view of another alternate elongate guide member component;

FIG. 5 is a perspective view of a second embodiment of a surgical instrument together with an orthopaedic implant, with part of the distal end of the elongate guide member component of the surgical instrument shown in cross-section, shown with the orthopaedic implant and implant carrier in a retracted position;

FIG. 6 is a perspective view of the surgical instrument and orthopaedic implant of FIG. 5, shown with the orthopaedic implant and implant carrier in an extended position;

FIG. 7 is a perspective view of the implant carrier component of the surgical instrument of FIGS. 5-6, shown disassembled from the elongate guide member component and without any orthopaedic implant;

FIG. 8 is a perspective view of the elongate guide member component of the surgical instrument of FIGS. 5-6, shown disassembled from the implant carrier of the surgical instrument;

FIG. 9 is a distal end view of the surgical instrument and orthopaedic implant of FIG. 5;

FIG. 10 is a perspective view of a third embodiment of a surgical instrument together with an orthopaedic implant, with part of the distal end of the elongate guide member component shown in cross-section and with the orthopaedic implant and implant carrier shown in a retracted position;

FIG. 11 is a perspective view of the surgical instrument of FIG. 10, shown with the implant carrier component and orthopaedic implant in an extended position;

FIG. 12 is a perspective view of a fourth embodiment of a surgical instrument, with part of the distal end of the elongate guide member component shown in cross-section and with the implant carrier and reciprocable member shown in a retracted position;

FIG. 13 is a perspective view of the surgical instrument of FIG. 12 shown with the implant carrier and reciprocable member in an extended position;

FIG. 14 is a perspective view of a fifth embodiment of a surgical instrument together with an orthopaedic implant, shown with the implant carrier and orthopaedic implant in a retracted position;

FIG. 15 is a perspective view of the surgical instrument and orthopaedic implant of FIG. 14, shown with the implant carrier and orthopaedic implant in an extended position;

FIG. 16 is a side elevation of a sixth embodiment of a surgical instrument, shown with the implant carrier in a retracted position;

FIG. 17 is a side elevation of the surgical instrument of FIG. 16, shown with the implant carrier in an extended position;

FIG. 20 is an enlarged cross-section of the distal end of the sixth embodiment of the surgical instrument with the implant carrier in the retracted position as shown in FIGS. 16 and 18;

FIG. 21 is an enlarged cross-section of the distal end of the sixth embodiment of the surgical instrument with the implant carrier in the extended position as shown in FIGS. 17 and 19;

FIG. 24 is an enlarged cross-section of the distal end of a surgical instrument similar to that shown in FIG. 22, shown with an alternative design for an implant carrier;

FIG. 25 is an enlarged cross-section of the distal end of the surgical instrument and orthopaedic implant of FIG. 24, shown with the implant carrier and orthopaedic implant in an extended position;

FIG. 26 is a perspective view of another embodiment of a surgical instrument with the elongate guide member component and actuator handle shown in longitudinal cross-section, showing an alternative implant carrier component in a retracted position, the perspective being from the proximal end of the surgical instrument;

FIG. 27 is an enlarged view of the distal end portion of the surgical instrument of FIG. 26;

FIG. 28 is a view similar to that of FIG. 26, shown with the implant carrier component in an extended position;

FIG. 29 is a perspective view of the surgical instrument of FIGS. 26-28, with the implant carrier shown in an extended position, the perspective being from the distal end of the surgical instrument;

FIG. 30 is an enlarged view of the distal end portion of the surgical instrument of FIG. 29;

DETAILED DESCRIPTION OF THE ILLUSTRATED EMBODIMENTS

Figure 31:
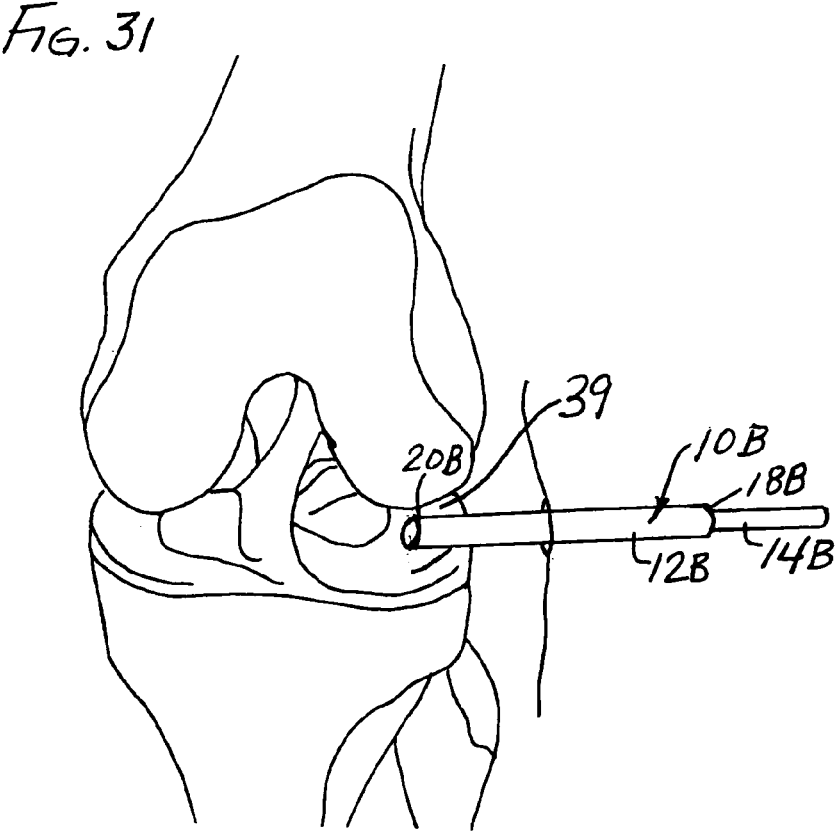
FIG. 31 is a diagrammatic representation of a human knee joint, showing the distal end of the surgical instrument of FIGS. 5-9 inserted through an arthroscopic surgery portal into the intra-articular space of the knee, with the implant carrier and orthopaedic implant in a retracted position.
Figure 32:
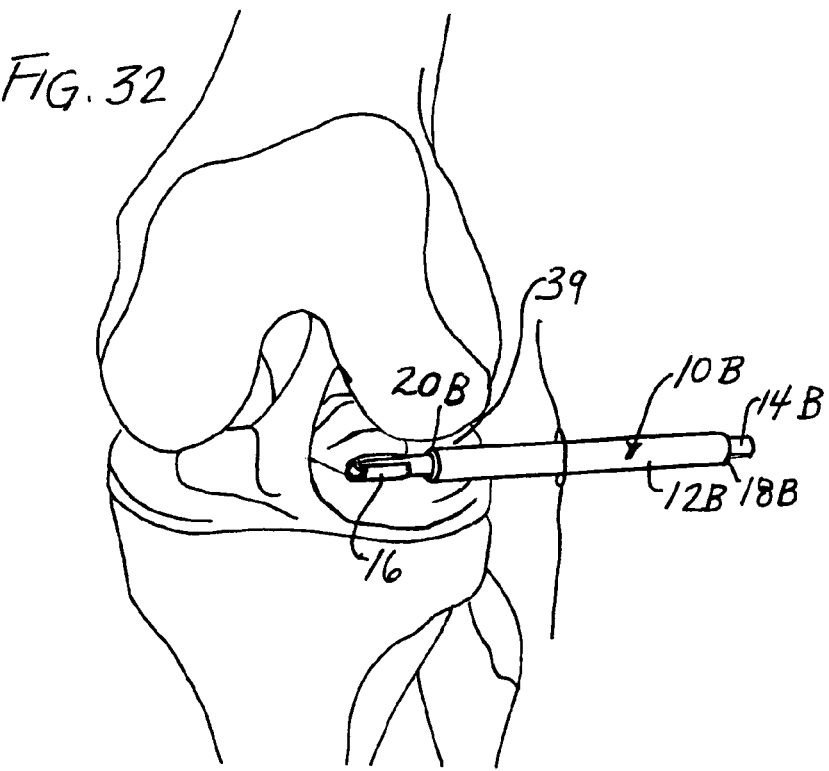
FIG. 32 is a diagrammatic representation of a human knee joint similar to FIG. 31, but with the implant carrier and orthopaedic implant in the extended position.
Figure 33:
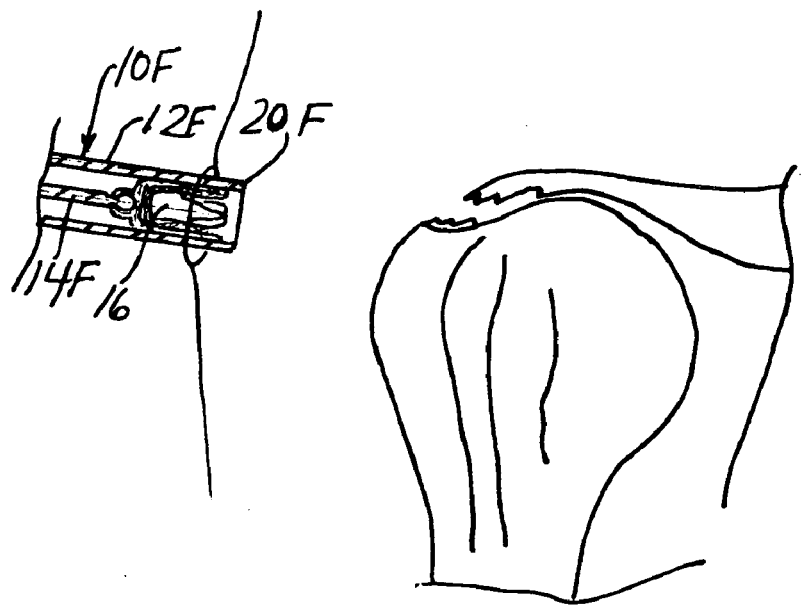
FIG. 33 is a diagrammatic representation of a human shoulder, showing the distal end of the surgical instrument of FIGS. 16-23 inserted through an arthroscopic surgery portal into the damaged area of the shoulder joint, with the implant carrier and orthopaedic implant in a retracted position.
Figure 34:
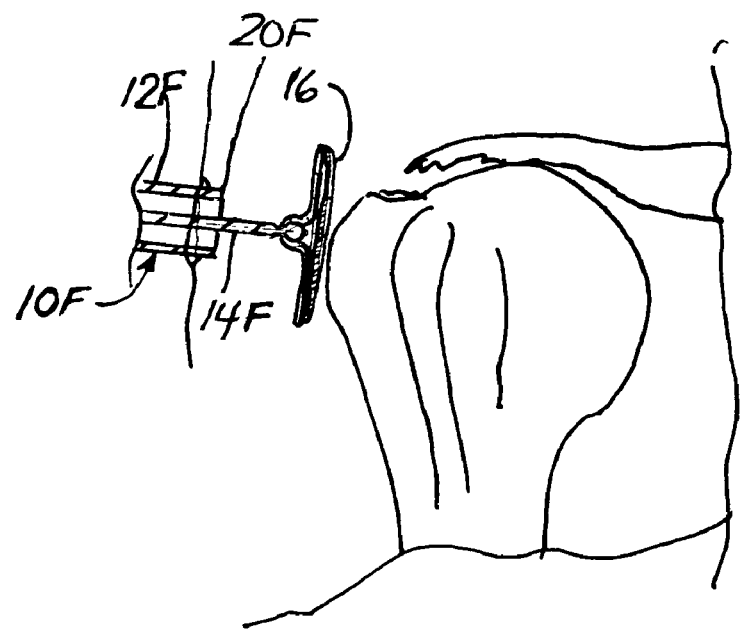
FIG. 34 is a diagrammatic representation of a human shoulder similar to FIG. 33, but with the implant carrier and orthopaedic implant in the extended position.
Figure 35:
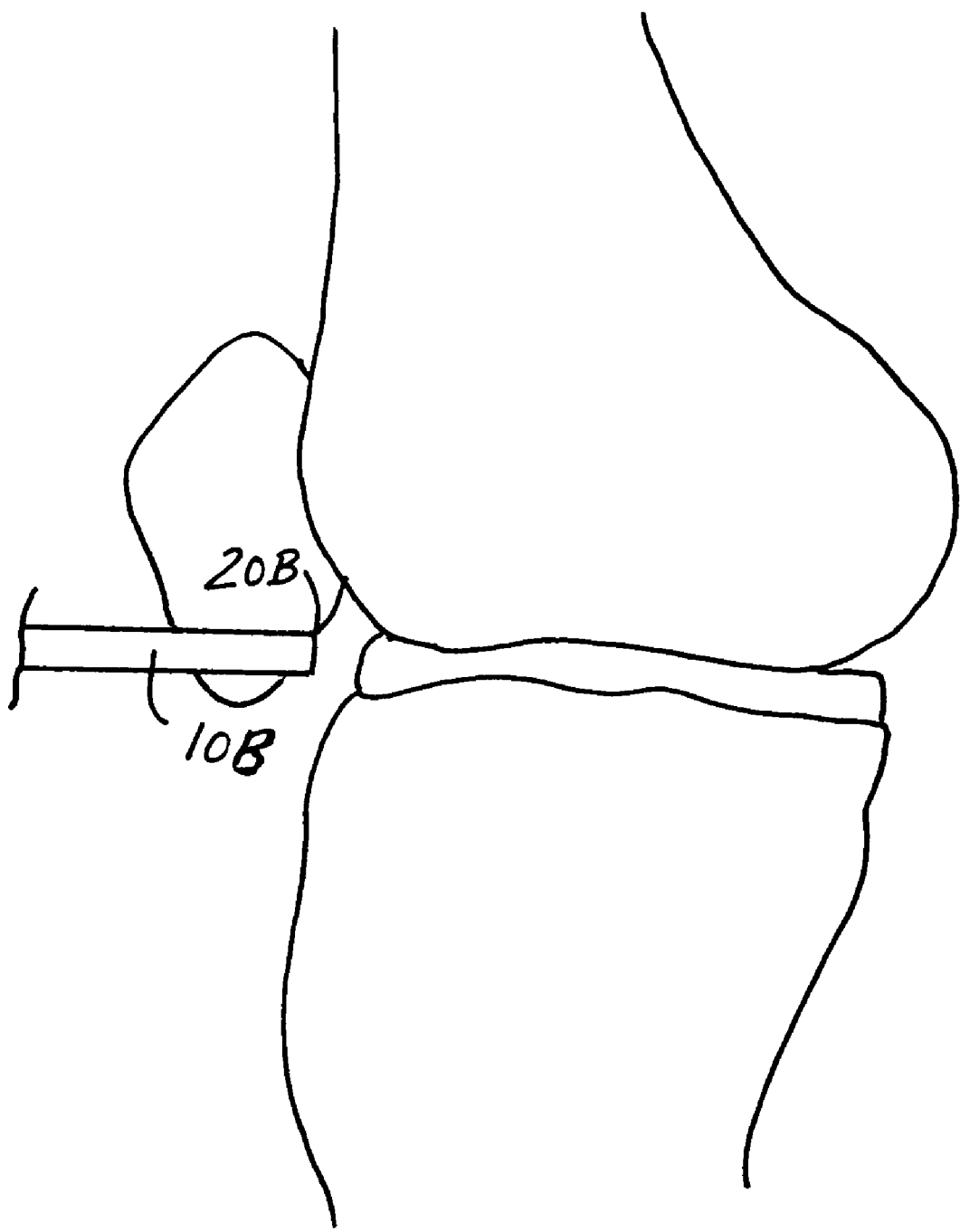
FIG. 35 is a diagrammatic representation of a human knee joint similar to FIG. 31, from the side.

The instrument of the present invention is useful in delivering an orthopaedic implant, as defined above, to a damaged joint site in the body. The joint site may for example be the knee, where the instrument can be used to deliver an orthopaedic implant for use in approximating, repairing or regenerating a diseased or damaged meniscus. FIGS. 31-32 illustrates the use of one embodiment of the present invention in delivering an orthopaedic implant to an intra-articular site in the knee. The intra-articular site may be in other locations in the body, such as the temporomandibular joint, between vertebrae, or any site where there is fibrocartilage in need of approximation, repair or regeneration. The instrument of the present invention can also be used to deliver an orthopaedic implant to a location outside of the intra-articular space of a joint site. For example, the instrument of the present invention can be used to deliver an orthopaedic implant to the area of the rotator cuff of the shoulder joint site. FIGS. 33-34 illustrate use of another embodiment of the present invention in delivering an orthopaedic implant to the area of a damaged rotator cuff in the shoulder. Unless expressly limited in the claims, "joint site" as used herein is intended to include the intra-articular space and other areas near the bones comprising a joint. "Damaged joint site", unless expressly limited in the claims, is intended to mean such a joint site that requires surgical repair, whether due to injury, degeneration or disease.

The instrument of the present invention may also find utility in delivering an implant to damaged tissue sites other than the joints. "Damaged tissue site", unless expressly limited in the claims, is intended to mean a tissue site that requires surgical repair, whether due to injury, degeneration or disease.

Several embodiments of the instrument of the present invention are illustrated in the accompanying drawings. The first embodiment of the instrument is designated 10A, the second embodiment is designated 10B, the third embodiment is designated 10C, the fourth embodiment 10D, the fifth embodiment 10E, the sixth embodiment 10F, the seventh embodiment 10G and the eighth embodiment 10H. All of these embodiments 10A, 10B, 10C, 10D, 10E, 10F, 10G, 10H share common components: they all include an elongate guide member 12 and an elongate reciprocable member 14. In each of the illustrated embodiments, the reciprocable member 14 is received in a telescoping manner within the elongate guide member.

The specific structures for each of these common components and other components of the surgical instruments may vary from embodiment to embodiment, as described in more detail below. In the drawings and in the following description, reference numbers for components of the different embodiments are generally followed by one or more of the letter references "A", "B", "C", "D", "E", "F", "G" and "H", referring to the particular embodiment or embodiments discussed and illustrated. In general, components with the same number reference and different letter references are similar. The use of a reference number followed by two reference letters separated by a hyphen indicates a series including all letters between the two stated reference letters; for example, 10A-10H refers to 10A, 10B, 10C, 10D, 10E, 10F, 10G and 10H. In addition, unless a difference in structure, function or operation is emphasized for a component, it should be understood that descriptions for the various components or parts apply to all of the parts identified with the same reference number.

The elongate reciprocable member 14A-14H in each of the embodiments 10A-10H functions to move an orthopaedic implant, shown at 16 in FIGS. 1-2, 5-6, 9-11, 14-15, 22-25 and 32-34, from a retracted position to an extended position. In the retracted position, the distal end of the reciprocable member 14A-14H and the orthopaedic implant 16 are between the proximal end 18 and distal end 20 of the elongate guide member 12A-12H. In the extended position, the distal end of the elongate reciprocable member is beyond the distal end 20 of the elongate guide member 12A-12H, and is capable of being positioned at the damaged joint site as shown in FIGS. 32 and 34. The elongate reciprocable member 14A-14H and orthopaedic implant 16 have a path of travel between the retracted position and extended position. At least part of the reciprocable member 14A-14H, and in some embodiments the orthopaedic implant 16 as well, are movable along the path of travel in both the proximal direction 22 and the distal direction 23. These directions of the path of travel are shown in FIGS. 1-2, 5-6, 10-19, 21 and 23-30.

The orthopaedic implant 16 can be of varying shapes and sizes. For example, the orthopaedic implant 16 can comprise a generally rectangular sheet as shown in FIG. 2A, with a length shown at $d_1$, a width shown at $d_2$, a thickness shown at $d_3$, and a diagonal dimension shown at $d_4$. The orthopaedic implant 16 can have a pillow or pouch of additional material, such as shown at 17 in FIGS. 1-2B. This additional material can comprise, for example: extracellular matrix material; bioactive agents, biologically-derived agents, cells, a biological lubricant, a biocompatible synthetic or a biocompatible inorganic material, for example. Many such orthopaedic implants are flexible, particularly when hydrated. Thus, the orthopaedic implant 16 can be temporarily deformed as the implant is placed in the elongate guide member 12A-12H. For example, the orthopaedic implant 16 can be rolled into a generally cylindrical shape as shown in FIG. 2B, so that the maximum width of the implant is reduced to the dimension shown at $d_5$ in FIG. 2B. Alternatively, the orthopaedic implant 16 can be folded over one or more times as shown in FIG. 2C, to reduce the width or length of the orthopaedic implant; in FIG. 2C, the overall length of the implant has been reduced to the dimension shown at $d_6$ by folding the implant. When the orthopaedic implant 16 has been delivered to the damaged joint site, the implant can be unrolled or unfolded to its full size, returning the implant to the original shape, such as the shape shown in FIG. 2A. It should be understood that the illustrated shapes of orthopaedic implants are provided as examples only; the present invention is not limited to any particular shape of orthopaedic implant unless expressly called for in the claims.

Values for the dimensions for the orthopaedic implant may be as follows: $d_1=25$ mm; $d_2=15$ mm; $d_3=1$ mm; $d_4=20$ mm; $d_5=10$ mm and $d_6=12$ mm. It should be understood that these dimensions are given as examples only; the present invention is not limited to any particular size of orthopaedic implant unless expressly called for in the claims. It should also be understood that the dimensions of the orthopaedic implant will depend somewhat on its intended end use; for example, a typical orthopaedic implant for use in rotator cuff repair could have a larger surface area than an orthopaedic implant for use in meniscal repair, although the meniscal repair implant could in some instances have a greater thickness.

With the reduced dimensions provided by temporarily deforming the shape of the orthopaedic implant, the implant can fit within the interior of the hollow elongate guide member 12A-12H. The elongate guide member 12A of the first surgical instrument 10A comprises a hollow tube open at both the proximal end 18A and distal end 20A. The interior surface 13A of the elongate guide member 12A has an inner transverse dimension shown at $d_7$ in FIGS. 4-4D. Although the length $d_1$ and width $d_2$ of the orthopaedic implant 16 can be greater than the maximum inner transverse dimension $d_7$ if the orthopaedic implant is in its natural shape (FIG. 2A), the implant can be deformed until the dimension $d_5$ or $d_6$ is less than the inner transverse dimension $d_7$ of the elongate guide member 12A so that the implant can be received in the elongate guide member.

The elongate guide member 12A illustrated in FIGS. 1-2 and 4-4D generally comprises a tube or cannula open at both proximal and distal ends 18A, 20A, with the outer surface and inner surface 13A being circular in shape when viewed from either the proximal end 18A or distal end 20A. It should be understood that this shape is provided as an example only; variations in the shape of the elongate guide member are possible, and the invention should not be considered to be limited to a particular shape unless expressly set forth in the claims. For example, instead of the outer surface forming a closed cylinder, the elongate guide member 12A could have a slot 32 as shown in FIG. 4B. Instead of being circular in shape when viewed from one of the ends, the elongate guide member 12A could have an elliptical shape when viewed from the proximal end or distal end, as shown in FIGS. 4C and 4D, and could also have a slot 32 as shown in FIG. 4D. Other shapes can also be used, such as the shape illustrated in FIGS. 14-15. The elongate guide member 12A could also have other features, such as an actuator handle as described below with respect to the surgical instruments 10F and 10H. In addition, although the illustrated elongate guide members 12A-12H generally comprise integral structures, it should be understood that assemblies could be used as well.

In the embodiments of FIGS. 5-30, the elongate reciprocable member 14B-14H includes an implant carrier portion 24B and a pusher portion 26B. The implant carrier portion 24B, 24C, 24E and pusher portion 26B, 26C, 26E can be integral, as in the surgical instruments 10B, 10C and 10E of FIGS. 5-11 and 14-15. The implant carrier portion 24D, 24F, 24G, 24H and pusher portion 26D, 26F, 26G, 26H can also be discrete elements as in the surgical instruments 10D, 10F, 10G and 10H, as shown in FIGS. 12-13 and 16-30. The discrete implant carrier 24F, 24G, 24H and pusher 26F, 26G, 26H can be connected to form an assembly, as in the surgical instruments 10F, 10G and 10H, as shown in FIGS. 16-30, or could be separate components of the surgical instrument, as in the surgical instrument 10D of FIGS. 12-13. In addition, the reciprocable member of the surgical instrument need not include an implant carrier; in the first illustrated surgical instrument 10A of FIGS. 1-4, the reciprocable member 14A is defined by a pusher 26A element alone; there is no implant carrier in the first illustrated surgical instrument 10A.

In the first illustrated surgical instrument 10A, the pusher 26A of the reciprocable member 14A comprises a shaft 28A and an enlarged diameter head 30A at the distal end of the shaft. In the illustrated embodiment, the shaft 28A has a length of about 6 inches and a diameter of about 12 mm; the length of the shaft 28A is generally long enough so that the surgeon can grasp at least the distal end of the shaft both when the reciprocable member 14A is in the retracted position (FIG. 1) and the extended position (FIG. 2); thus the shaft 28A is longer than the elongate guide member 12A. The head 30A of the reciprocable member 14A has an outer diameter shown at $d_8$ in FIG. 3. In the first illustrated embodiment, $d_8$ is slightly less than the inner transverse dimension $d_7$ of the elongate guide member 12A. The shape of the head 30A is generally circular in end view in the embodiment of FIG. 3, to complement the shape of the inner surface 13A of the elongate guide member 12A. If the elongate guide member has a different shape, such as an elliptical shape in transverse cross-section, the head 30A may be oval shaped to complement the shape of the inner surface of the elongate guide member.

Examples of values for the dimensions for the surgical instrument 10A may be as follows: $d_7$=10.5 mm and $d_8$=10 mm. The wall of the illustrated elongate guide member 12A has a total thickness of about 1.5 mm. Generally, it may be preferable to size the instruments so that they can be introduced through a typical arthroscopic portal if desired. Typical arthroscopic portals have a length of about 8-12 mm. However, the surgical instrument 10A can also be used in a minimally invasive procedure, such as a mini-arthrotomy, as well as in an open arthrotomy or other orthopaedic surgical procedure. The instruments could have larger sizes for use in these other procedures. In addition, it should be understood that the present invention is not limited to any particular dimension unless expressly called for in the claims.

To use the first illustrated surgical instrument 10A, the surgeon would first place the distal end 20A of the elongate guide member 12A at the damaged joint site. This step may be performed arthroscopically if desired. The surgeon would then fold or roll the orthopaedic implant 16 so that the implant can be inserted into the proximal end 18A of the elongate guide member 12A. With the reciprocable member 14A disassembled from the elongate guide member 12A, the surgeon would then insert the orthopaedic implant 16 into the proximal end 18A of the elongate guide member 12A and then insert the head 30 of the reciprocable member 14A into the proximal end 18A of the elongate guide member 12A. The reciprocable member 14A and orthopaedic implant would then be in a retracted position, such as that shown in FIG. 1. The surgeon would then push the reciprocable member 14A through the elongate guide member 12A toward the distal end 20A, so that the head 30A pushes the orthopaedic implant 16 in a distal direction until the orthopaedic implant 16 is pushed out the distal end 20A of the elongate guide member 12A and thereby delivered to the damaged joint site. At this point of the procedure, the surgical instrument 10A and orthopaedic implant 16 would be in the extended position illustrated in FIG. 2. The surgeon can then pull the reciprocable member 14A in a proximal direction and remove it from the elongate guide member 12A, leaving the elongate guide member in place for use with other instruments if desired; alternatively, the surgeon can pull both the reciprocable member and the elongate guide member in a proximal direction to remove both components of the instrument from the surgical site. In the first illustrated surgical instrument 10A, the inner surface 13A of the elongate guide member 10A is preferably smooth to enable the orthopaedic element to be slid along the inner surface 13A easily and without damage. The elongate guide member 12A and the reciprocable member 14A can both be made of a surgical grade plastic, such as medical grade ABS, for example. However, unless expressly called for in the claims, the present invention is not limited to any particular material for any of the components of the surgical instrument.

Thus, the orthopaedic implant 16 is delivered to the damaged joint site while protected from damage by the elongate guide member 12A.

After the orthopaedic implant 16 has been delivered to the damaged joint site, the surgeon may unfold or unroll the implant to restore it to its original shape. The surgeon can then secure the implant in place at the damaged joint site. The surgeon may use the device disclosed in U.S. patent application Ser. No. 10/609,768 (now U.S. Pat. No. 7,473,259 issued Dec. 17, 2008), entitled "Implant Stabilizing Instrument, Kit and Method," filed concurrently herewith by Andrew M. Jacobs, Carolyn K. Day, Rhonda B. Clarke, Herbert E. Schwartz, John W. Kemppainen, Prasanna Malaviya and Anthony D. Zannis, which is incorporated by reference herein in its entirety. The instrument, kit and method disclosed in that patent application may be used to move and stabilize the implant while securing the implant to the native tissue.

In the second illustrated surgical instrument 10B, the elongate guide member 12B may be of the same construction and size as that of the first surgical instrument 10A, and may be shaped as illustrated in FIGS. 4-4D. The second surgical instrument 10B differs from the first surgical instrument 10A primarily in the features and operation of the reciprocable member 14B. In the second surgical instrument 10B, the reciprocable member 14B comprises a hollow tube and includes an implant carrier 24B at its distal end and a pusher 26B extending proximally from the implant carrier to the proximal end of the reciprocable member 14B. In this embodiment, the reciprocable member 14B is an integral component: the implant carrier 24B and pusher 26B are integral parts of the elongate reciprocable member 14B.

As shown in FIG. 7, the implant carrier portion 24B of the elongate reciprocable member 14B of the second instrument 10B has a pair of spaced longitudinal slots 34, 36 at its distal end, defining an integral arm 38 between the slots 34, 36. As shown in FIGS. 5-6 and 9, the orthopaedic implant 16 can be temporarily fixed to the distal end of the reciprocable member 14B by wrapping the orthopaedic implant around the outer circumference of the elongate reciprocal member at the implant carrier 24B. Part of the implant is inserted in each of the slots 34, 36 so that part of the implant is in the interior of the reciprocable member beneath the arm 38, thereby temporarily securing the implant to the implant carrier portion 24B of the reciprocable member 14B.

The elongate reciprocable member 14B may be made of any standard surgical grade material, such as a surgical grade plastic. An example of a suitable material is medical grade ABS. The elongate reciprocable member 14B may have a wall thickness of about 1-2 mm, an inner diameter of 8 mm and an outer diameter of 10 mm. The slots 34, 36 may have a length of about 25 mm and a width of about 2 mm, and the arm 38 may have a length of about 2 mm and a width of about 4 mm. It should be understood that this material and these dimensions are provided as examples only; the present invention is not limited to this material or dimension unless expressly set forth in the claims.

The implant carrier 24B provides a structure to which the orthopaedic implant 16 can be temporarily secured and moved from a point outside of the body to a joint site, and more particularly to a damaged joint site. Providing such an implant carrier is advantageous in protecting the implant as it is moved to the damaged joint site, particularly where the damaged joint site is in an intra-articular space. First, any force necessary to move the implant can be exerted on the implant carrier 24B rather than on the orthopaedic implant itself. Second, since the implant carrier is in a retracted position within the elongate guide member as the distal end of the elongate guide member is moved to the damaged joint site, the orthopaedic implant is protected from damage as it is moved into the damaged joint site. Providing such an implant carrier also gives the surgeon some flexibility: the orthopaedic implant can be delivered to the damaged joint site in either a wet or dry condition.

To use the second illustrated instrument 10B, the surgeon would wrap the orthopaedic implant around the outer surface of the implant carrier portion 24B of the reciprocable member 14B and tuck a portion of the implant through the slots 34, 36 and under the arm 38. The remainder of the surgical procedure would be similar to that described above for the first illustrated instrument 10A.

FIG. 31 illustrates the second instrument 10B with the distal end 20B of the elongate guide member 12B in position at the damaged joint site. In FIG. 31, the damaged joint site is the intra-articular space of the knee, shown generally at 39. FIG. 32 illustrates the second instrument 10B with the implant carrier 24B in the extended position at the damaged joint site 39. Once the orthopaedic implant has been delivered to the damaged joint site 39, the surgeon may use standard surgical instruments, such as forceps, to remove the orthopaedic implant 16 from the implant carrier 24B and place the implant at the desired position at the damaged joint site, such as along the site of a meniscectomy. It should be understood that the second illustrated instrument can be used to deliver orthopaedic implants to other damaged joint sites as well. The present invention is not limited to any particular site unless expressly set forth in the claims.

The implant carrier 24B is movable along the elongate guide member 12B in both a proximal-distal direction and a distal-proximal direction. The elongate guide member 12B defines the path of travel of the implant carrier 24B. In addition, together the elongate guide member 12B and the implant carrier 24B are shaped to protect the orthopaedic implant from damage from tissue or other internal obstacles, which could otherwise tear, or damage the implant.

The third illustrated surgical instrument 10C shares features of both the first and second illustrated instruments 10A, 10B. The elongate guide member 12C can be substantially the same as those described above for the first and second instruments 10A, 10B. The elongate reciprocable member 14C of the third illustrated surgical instrument 10C comprises an elongate rod pusher portion 26C and an implant carrier portion 24C.

The implant carrier portion 24C of the third illustrated instrument 10C comprises a flexible enlarged portion of the distal end of the elongate reciprocable member 14C. The flexibility of the implant carrier portion 24C allows it to elastically deform to conform to the shape of the curved interior surface of the elongate guide member 12C when in the retracted position as shown in FIG. 10. Thus, when in the retracted position of FIG. 10, the implant carrier portion 24C has a maximum transverse dimension less than or equal to the inner diameter $d_7$ of the elongate guide member 12C. When the implant carrier portion 24C is in the deformed, curved shape shown in FIG. 10, the orthopaedic implant 16 will roll into a shape like that shown in FIG. 2B, reducing the maximum transverse dimension of the orthopaedic implant. When the reciprocable member 14C is extended so that the implant carrier portion 24C extends beyond the distal end of the elongate guide member 12C, the implant carrier portion 24C springs back to its enlarged shape, as shown in FIG. 11, where its maximum transverse dimension is that shown at $d_9$ in FIG. 11. The orthopaedic implant also springs back to its original shape as shown in FIG. 11, where its maximum transverse dimension is greater than the maximum transverse dimension $d_7$ of the inner surface of the elongate guide member 12C. As with the first and second surgical instruments 10A, 10B, the third surgical instrument 10C allows for delivery of an orthopaedic implant larger than the maximum transverse dimension of the elongate guide member 12C to the damaged joint site.

In the third surgical instrument 10C, the implant carrier portion 24C has a plurality of spaced, small through-holes, shown at 42 in FIG. 10. The orthopaedic implant 16 can be temporarily secured to the implant carrier portion 24C by suturing the implant to the implant carrier. Such sutures are shown at 44 in FIGS. 10-11.

Any surgical grade material with elastic properties can be used for the implant carrier portion 24C of the third surgical instrument 10C. An example of a suitable material is shape-memory plastic. A commercially available flexible shape memory material such as the Nitinol alloy of nickel and titanium can also be used. However, it should be understood that this material is provided as an example only; the invention is not limited to use of any particular material unless expressly set forth in the claims.

In the third illustrated surgical instrument 10C, the implant carrier portion 24C of the reciprocable member 14C is integral with the pusher portion 26C. However, it should be understood that these two portions could comprise discrete elements assembled to form the reciprocable member 14C.

In the third illustrated surgical instrument 10C, the pusher portion 26C of the reciprocable member 14C comprises a solid elongate rod, similar to the pusher portion 26A of the first illustrated instrument 10A. However, the pusher portion 26C of either embodiment could be a hollow tube as well.

Use of the third illustrated surgical instrument 10C is similar to that described above for the first two illustrated surgical instruments 10A, 10B. In using the third surgical instrument 10C, the surgeon would suture the orthopaedic implant 16 to the implant carrier portion 24C of the reciprocable member 12C and then deliver the implant to the damaged joint site by pushing the pusher portion 26C of the reciprocable member 12C and implant through the elongate guide member 12C. At the damaged joint site, the implant carrier 24B would spring into its expanded shape shown in FIG. 11. The surgeon can use standard surgical instruments to cut the sutures 44 and move the orthopaedic implant from the implant carrier 24C to the desired site at the joint.

The fourth illustrated surgical instrument 10D shares many features with those of the first three illustrated surgical instruments 10A, 10B, 10C. As shown in FIGS. 12-13, the pusher portion 26D of the reciprocable member 14D is essentially the same as that described above for the first surgical instrument 10A. As shown in FIGS. 12-13, the distal end 20D of the elongate guide member 12D of the fourth illustrated surgical instrument 10D includes an annular shoulder 45; the remainder of the elongate guide member 12D is essentially the same as those described above for the first three illustrated instruments 10A, 10B, 10C. In the embodiment of FIGS. 12-13, the surgical instrument 10D includes a discrete implant carrier 24D that is not connected to the pusher 26D. The illustrated discrete implant carrier 24D includes a cylindrical proximal portion 46 and integral opposing clip arms 48, 50 extending axially from the cylindrical portion. The cylindrical portion 46 has an outer diameter slightly less than the inner diameter of the elongate guide member, and an axial length great enough to provide stability to the implant carrier 24D within the elongate guide member 12D. As shown in FIG. 13, the annular shoulder 45 of the elongate guide member 12D and the cylindrical portion 46 of the implant carrier 24D cooperate to prevent the implant carrier 24D from fully exiting from the distal end 20D of the elongate guide member 12D. In the fully extended position, only the opposing clip arms 48, 50 of the implant carrier 24D extend beyond the distal end 20D of the elongate guide member 12D.

The discrete implant carrier 24D of the fourth illustrated instrument 10D may be made of any standard surgical grade material. It may be desirable for the clip arms 48, 50 to be made of a flexible material such as spring stainless steel for example. However, the present invention is not limited to any particular material or property of material unless expressly set forth in the claims.

In using the fourth illustrated surgical instrument 10D, the surgeon would place part of the orthopaedic implant between the two opposing clip arms 48, 50 of the implant carrier 24D and then place the combination of the implant carrier 24D and orthopaedic implant 16 into the proximal end 18D of the elongate guide member 12D, with the implant and clip arms facing the distal end 20D of the elongate guide member 12D. Next, the pusher 26D is inserted into the proximal end 18D of the elongate guide member 12D so that the head 30D of the pusher 26D is nearest the cylindrical portion 46 of the implant carrier 24D. With the implant carrier 24D in the retracted position shown in FIG. 12, the distal end 20D of the elongate guide member 12D is inserted at the damaged joint site, and the pusher 26D is pushed in a distal direction to thereby push the insert carrier 24D distally until the clip arms 48, 50 and orthopaedic implant are in the extended position shown in FIG. 13. The surgeon can then use standard surgical instruments such as forceps at the damaged joint site to remove the orthopaedic implant from between the clip arms 48, 50 and place the implant at the desired site for permanent attachment to the native soft tissue.

As with the other illustrated surgical instruments 10A-10C and 10E-10H, use of the fourth illustrated surgical instrument 10D allows for delivery of an orthopaedic implant larger than the maximum transverse dimension of the elongate guide member 12D to the damaged joint site. And as with the other illustrated surgical instruments 10A-10C and 10E-10H, the fourth illustrated surgical instrument 10D protects the orthopaedic implant from damage from tissue or other internal obstacles as the implant is delivered from outside the body to the damaged joint site.

In the fifth illustrated surgical instrument 10E shown in FIGS. 14-15, the elongate guide member 12E comprises a slide, open at the top. The slide has guide channels 52, 54 along its side edges. The maximum transverse inner dimension $d_7$ of the slide is the transverse distance between these channels 52, 54. The reciprocable member 14E of the fifth illustrated instrument 10E comprises an integral implant carrier portion 24E and pusher portion 26E. The implant carrier portion 24E comprises a covered box open on the distal side. The implant carrier portion 24E has side edges 56, 58 received and slidable within the guide channels 52, 54 of the elongate guide member 12E when the implant carrier is in the retracted position shown in FIG. 14. The pusher portion 26E comprises a thin flexible sheet with side edges received within the guide channels 52, 54 of the elongate guide member 12E.

The elongate guide member 12E of the fifth illustrated instrument 10E can have other shapes. Reference is made to U.S. patent application Ser. No. 10/610,287, entitled "Slide and Kit for Delivering Implants", filed concurrently herewith by Thomas S. Camino, Anthony D. Zannis, John W. Kemppainen and Herbert E. Schwartz. The shapes of the pusher portion 26E and the implant carrier portion 24E of the fifth illustrated instrument may be varied from those illustrated in FIGS. 14-15 to complement the shape of the elongate guide member 12E.

Use of the fifth illustrated instrument 10E is similar to that described above for the second illustrated surgical instrument 10B. The orthopaedic implant can be folded or rolled and then placed in the implant carrier portion 24E for delivery from outside of the body to the damaged joint site. After the distal end 20E of the elongate guide member 12E is introduced at the damaged joint site, the side edges 56, 58 of the implant carrier portion 24E can be inserted within the channels 52, 54 at the proximal end 18E of the elongate guide member outside the body. The surgeon can then push the implant carrier portion 24E and implant along the length of the elongate guide member 12E until the implant carrier portion 24E is at the damaged joint site. The surgeon can then use standard surgical instruments to remove the implant from the implant carrier portion 24E and secure the implant at the damaged joint site.

As with the other illustrated surgical instruments 10A-10D and 10F-10H, use of the fifth illustrated surgical instrument 10E allows for delivery of an orthopaedic implant larger than the maximum transverse dimension of the elongate guide member 12E to the damaged joint site. And as with the other illustrated surgical instruments 10A-10D and 10F-10H, the fifth illustrated surgical instrument 10E protects the orthopaedic implant from damage from tissue or other internal obstacles as the implant is delivered from outside the body to the damaged joint site.

A sixth embodiment of the surgical instrument of the present invention is illustrated in FIGS. 16-23. In the sixth illustrated instrument 10F, the elongate guide member 12F includes a hollow tube portion 60F and a handle portion 62F at the proximal end 18F of the elongate guide member 12F. The handle portion 62F has an enlarged diameter for the surgeon to hold, while the hollow tube portion 60F has an outer diameter that allows for use in arthroscopic surgical procedures, mini-arthrotomies or open arthrotomies. As best seen in FIGS. 16-17, the hollow tube portion 60F has a J-shaped slot 64F extending from the exterior to the interior surface. The J-shaped slot 64F has two axially-oriented segments 66F, 68F joined at their distal ends by a transverse segment 70F. The J-shaped slot 64F receives a pin 72F fixed to the reciprocable member 14F of the sixth illustrated instrument 10F.

Figure 18:
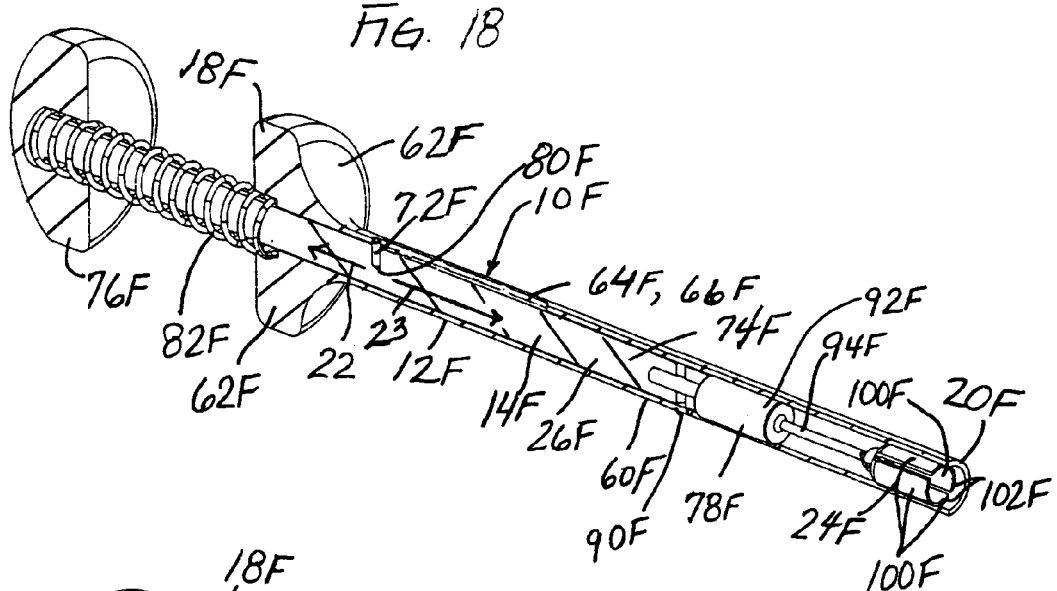
FIG. 18 is a view similar to FIG. 16, but with the elongate guide member component, shaft and actuator handle shown in longitudinal cross-section.
Figure 19:
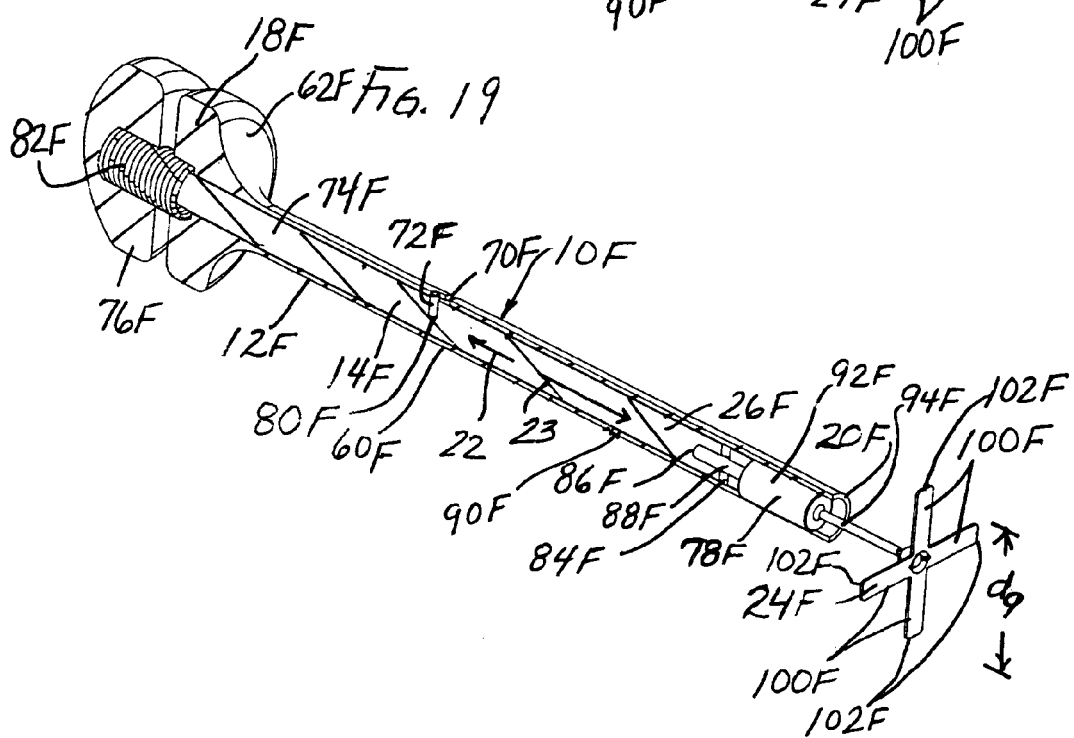
FIG. 19 is a view similar to FIG. 17, but with the elongate guide member component, shaft and actuator handle shown in longitudinal cross-section.

The reciprocable member 14F of the sixth illustrated instrument 10F comprises an assembly of four components. As best seen in FIGS. 18-19, these four components include an elongate cylindrical shaft 74F, an enlarged actuator 76F connected to the proximal end of the elongate cylindrical shaft 74F, a connector member 78F connected to the elongate cylindrical shaft 74F, and an implant carrier 24F connected to the connector member 78F.

As shown in FIGS. 17-19, the elongate cylindrical shaft 74F has an outside diameter that is slightly less than the inside diameter of the hollow tube portion 60F of the elongate guide member 14F to allow the elongate shaft 74F to be easily moved in the proximal and distal directions 22, 23 within the hollow tube portion 60F. Although the illustrated shaft 74F is cylindrical, it should be understood that the invention is not limited to complementary cylindrical shapes for the shaft 74F and inner surface of the tube 60F.

The elongate shaft 74F has a first radial bore 80F about midway between the proximal and distal ends of the shaft 74F; this radial bore 80F receives the pin 72F in an interference fit. The first radial bore 80F extends from the outer surface of the shaft inward. The length of the pin 72F is greater than the depth of the bore 80F so that an end of the pin is exposed beyond the outer surface of the shaft 74F. The length of the pin 72F is great enough to extend into the J-slot 64F of the tube portion 60F of the elongate guide member 14F. As the elongate shaft 74F is pushed in a distal direction, the pin 72F travels along the long axial segment 66F of the J-slot until the pin reaches the transverse segment 70F. By rotating the shaft 74F of the pusher 26F relative to the tube portion 60F of the elongate guide member 12F, the pin 72F can be moved along the short transverse segment 70F of the J-shaped slot 64 F until the pin 72F reaches the short axial segment 68F of the slot 64F. The shaft 74F can then be moved slightly in the proximal direction 22 relative to the tube 60F to move the pin 72F to the proximal end of the short axial segment 68F of the slot 64F.

The sixth surgical instrument 10F also includes a spring 82F positioned between the enlarged actuator 76F and the handle portion 62F of the elongate guide member 14F, urging these two components apart. As shown in FIGS. 18-19, the proximal end of the spring 82F is received in a complementary recess in the interior of the actuator 76F and the distal end of the spring 82F is received in a complementary recess in the interior of the handle portion 62F of the elongate guide member 12F. The spring surrounds a portion of the elongate shaft 74F near the proximal end of the shaft. The proximal end of the shaft 74F is fixed to the actuator 76F.

When the pin 72F is in the long axial segment 66F of the J-shaped slot 64F, the spring 82F urges the shaft 74F and the pin 72F in a proximal direction, until the pin 72F is at the proximal end of the long axial segment 66F of the slot 64F as shown in FIGS. 16 and 18, defining a retracted position of the reciprocable member 14F. When the pin 72F is at the proximal end of the short axial segment 68F of the J-shaped slot 64F, the reciprocable member 14F is in its extended position. Provision of the slot 64F and pin 72F allows the surgeon to lock the instrument in the extended position.

As shown in FIGS. 18-19, the shaft portion 74F of the reciprocable member 14F includes a transverse bore 84F near the distal end of the shaft and an axial bore 86F extending in a proximal direction from the distal end face of the shaft 74F. The transverse bore is threaded and extends diametrically through the shaft 74F and intersects the longitudinal bore 86F. The longitudinal bore 86F of the shaft 74F receives an axial proximal rod 88F portion of the connector member 78F. To fix the connector member 78F to the elongate shaft 74F, a set screw (not shown) may be inserted through a bore 90F (see FIGS. 16-19) in the hollow tube portion 60F of the elongate guide member 12F. The set screw is threaded into the bore 84F until it contacts the axial proximal rod portion 88F of the connector member 78F. The set screw is short enough so that no part of the screw extends past the outer surface of the elongate shaft 74F of the reciprocable member 14F; thus, the set screw does not interfere with movement of the reciprocable member 14F in the proximal and distal directions 22, 23.

The connector member 78F also includes a cylindrical body portion 92F and a distal axial rod portion 94F. The cylindrical body portion 92F has an outer diameter that is slightly smaller than the inner diameter of the tube portion 60F of the elongate guide member 14F to allow the cylindrical body portion 92F to move freely in the proximal and distal directions while providing stability to the distal end of the reciprocable member 14F. The cylindrical body portion remains within the tube portion 60F throughout the range of motion of the illustrated surgical instrument 10F. The distal axial rod portion 94F moves out the distal end of the tube portion 60F when the reciprocable member 14F is in the extended position shown in FIGS. 17, 19, 21 and 23. At the distal end of the distal axial rod portion 94F, the connector member 78F has a reduced diameter and a spherical end portion 96F.

The spherical end portion 96F of the distal axial rod portion 94F of the connector member 78 F is connected to the implant carrier portion 24F of the sixth illustrated surgical instrument 10F. The implant carrier portion 24F of the sixth instrument 10F comprises a base 98F and a plurality of arms 100F. In the sixth illustrated instrument 10F, the base 98F and arms 100F are integral. The base 98F has a spherical shape with an interior surface shaped to complement the spherical end portion 96F of the connector member 78F for mounting the implant carrier 24F to the connector member 78F.

Figure 22:
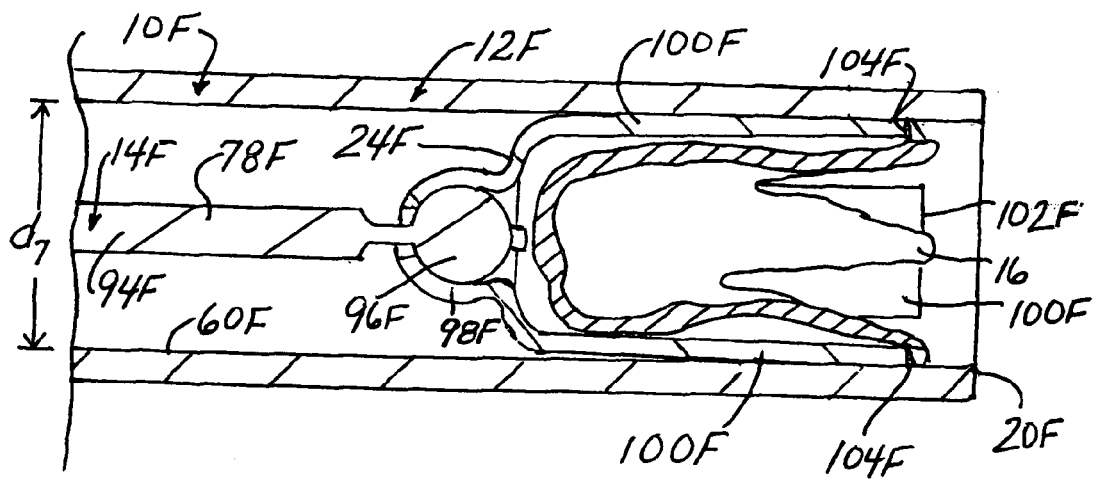
FIG. 22 is an enlarged cross-section similar to that shown in FIG. 20, with an orthopaedic implant temporarily secured to the implant carrier.
Figure 23:
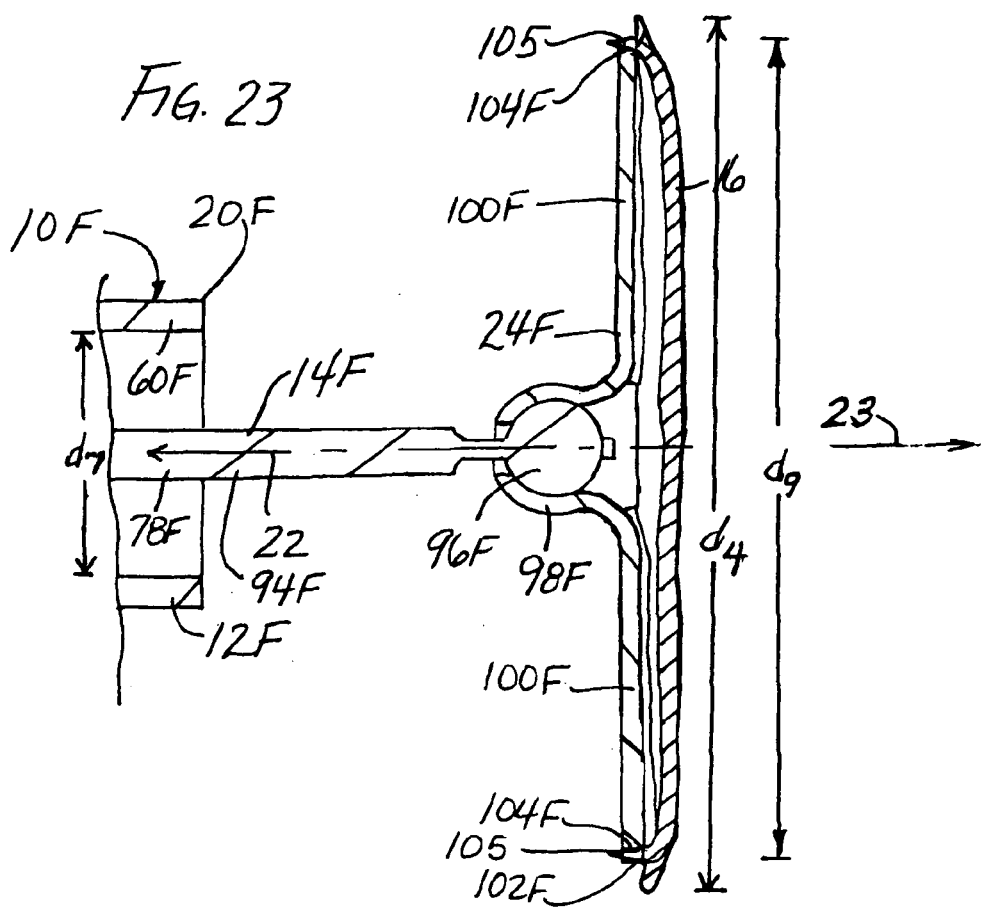
FIG. 23 is an enlarged cross-section similar to that shown in FIG. 21, with an orthopaedic implant temporarily secured to the implant carrier.

The arms 100F of the implant carrier portion 24F extend outwardly from the base 98F. In the illustrated embodiment, there are four arms 100F spaced evenly about the base 98F, although fewer or more arms could be used. The arms 100F have different shapes depending on the position of the arms relative to the tube portion 60F of the elongate guide member 12F. As shown in FIGS. 18, 20 and 22, the implant carrier portion 24F has a retracted position between the proximal end 18F and distal end 20F of the elongate guide member 12F. When in the retracted position, the arms 100F extend in a generally longitudinal direction; the free ends 102F of the arms 100F are directed toward the distal end 20F of the elongate guide member 12F. When in the extended position, the arms 100F extend outward from the base 98F in a radial direction, as shown in FIGS. 17, 19, 21 and 23.

In the sixth illustrated instrument 10F, the base 98F and arms 100F are made of a flexible material with elastic properties, such as a commercially available shape memory metal alloy like Nitinol (nickel-titanium alloy) or a suitable surgical grade polymer with such properties, such as shape-memory plastic. The natural shape of the base 98F and arms 100F is that shown in FIGS. 17, 19, 21 and 23, with the arms 100F extending radially outward from the base 98F. When the implant carrier portion 24F is moved in a proximal direction 22 into the elongate guide member 12F, the inner surface of the elongate guide member 12F deforms the arms 100F to the shape shown in FIGS. 18, 20 and 22, so that the arms 100F extend in a generally longitudinal direction. When the implant carrier portion is moved in a distal direction so that the arms 100F are free from the inner surface of the elongate guide member 12F, the elastic properties of the implant carrier portion 24F urge the arms 100F radially outward to the radially-expanded shape shown in FIGS. 17, 19, 21 and 23. Thus, in the retracted position, the maximum transverse dimension of the implant carrier portion 24F is less than the inner transverse dimension $d_7$ of the tube portion 60F of the elongate guide member 12F. In the extended position, the expanded transverse dimension $d_9$ of the implant carrier portion is substantially greater than the inner transverse dimension $d_7$ of the tube portion 60F of the elongate guide member 12F. For example, the expanded transverse dimension $d_9$ of the implant carrier portion 24F may be 20 mm; it should be understood that this dimension is provided as an example only, and the present invention is not limited to any particular value for the expanded transverse dimension $d_9$ unless expressly called for in the claims. It should also be understood that dimensions may be varied depending on the intended end use of the surgical instrument. For example, it may be desirable to provide an instrument with a larger expanded transverse dimension for instruments intended for use in the shoulder than in the knee, or for instruments intended for use in a mini-arthrotomy instead of in an arthroscopic procedure. Since the implant carrier portion 24F of the sixth illustrated instrument 10F is a discrete component, it may be desirable to provide different sizes of implant carriers in a surgical kit to accommodate different sizes of orthopaedic implants.

As shown in FIG. 20, the free ends 102F of the implant carrier portion 24F of the sixth illustrated surgical instrument 10F include cut-outs or notches 104F. These notches 104F function in securing the orthopaedic implant to the arms 100F of the implant carrier portion 24F. For example, if the orthopaedic implant has barbs 105 at its periphery for securing the implant to soft tissue at the damaged joint site in the body, the barbs 105 can be received in the notches 104F in a friction fit to temporarily secure the implant to the implant carrier portion. The notches 104F could also serve to receive sutures. It should be understood that the notches 104F are provided as an example of a structure that could be used to temporarily secure the orthopaedic implant to the implant carrier. The arms 100F could also or alternatively include, for example, holes to receive suture for temporarily securing the implant to the implant carrier.

The connection between the implant carrier portion 24F and the connector member 78F of the reciprocable member 14F can be varied from that illustrated. For example, the spherical end portion 96F could be part of the implant carrier 24F and the complementary hollow portion could be part of the connector member 78F.

If the surgical instrument 10F is to be used repeatedly in numerous surgical procedures, the connector member 78F can be made of a material that should withstand the stresses exerted on the connector member by the deformation of the implant carrier 24F as it is moved between the retracted and extended positions. For example, the connector member 78F can be made of a surgical grade metal such as surgical grade stainless steel. The shaft 74F can be made of the same or a different material since the shaft 74F will be subjected to less stress in use. For example, the shaft 74F can be made of a surgical grade polymer such as medical grade acetal. The shaft 74F and connector member 78F can also comprise an integral structure if desired.

In using the sixth illustrated surgical instrument 10F, the surgeon would push the enlarged actuator 76F in a distal direction and rotate the actuator 76F to move the pin 72F along the J-shaped slot 64F until the pin 72F is at the proximal end of the short axial segment 68F of the slot, thereby temporarily locking the implant carrier portion 24F in the extended position shown in FIGS. 17, 19, 21 and 23. The surgeon can then secure part of the orthopaedic implant to the arms 100F of the implant carrier portion 24F, such as by wrapping suture around the implant and arm or, if the implant includes structures such as barbs, by placing one barb 105 in each notch 104F. Once the implant is secure on the arms of the implant carrier, the surgeon can push slightly on the actuator 76F and twist the actuator 76F to release the pin 72F and allow the spring 82F to urge the actuator 76F away from the elongate guide member 12F to thereby move the shaft 74F in a proximal direction 22. As the shaft 74F is moved in the proximal direction 22, the implant carrier 24F is pulled into the interior of the tube portion 60F of the elongate guide member 12F. The inner surface of the tube portion 60F of the elongate guide member deforms the arms 100F of the implant carrier, pushing the arms 100F closer together so that the entire implant carrier 24F can fit within the tube portion 60F of the elongate guide member 12F. As the implant carrier 24F is temporarily deformed, the orthopaedic implant folds into a more compact shape to fit within the tube portion 60F of the elongate guide member 12F, as shown in FIG. 22.

With the implant carrier 24F in the retracted position shown in FIG. 22, the distal end 20F of the elongate guide member 12F is inserted at the damaged joint site, as shown for example in FIG. 33. Once the distal end 20F of the elongate guide member 12F is properly positioned at the damaged joint site, the surgeon can push on the actuator 76F to move the shaft 74F in a distal direction 23 until the implant carrier portion 24F is outside of the confines of the tube portion 60F of the elongate guide member 12F. Once released from the tube portion 60F, the elasticity or shape memory of the arms 100F urges the arms 100F to the extended position as shown in FIG. 34, thereby expanding the orthopaedic implant at the damaged joint site. The surgeon can then use standard surgical instruments such as forceps at the damaged joint site to remove the orthopaedic implant from the arms 100F of the implant carrier 24F and place the implant at the desired site for permanent attachment to the native soft tissue.

As with the other illustrated surgical instruments 10A-10E and 10G-10H, use of the sixth illustrated surgical instrument 10F allows for delivery of an orthopaedic implant larger than the maximum transverse dimension of the elongate guide member 12F to the damaged joint site. And as with the other illustrated surgical instruments 10A-10E and 10G-10H, the sixth illustrated surgical instrument 10F protects the orthopaedic implant from damage from tissue or other internal obstacles as the implant is delivered from outside the body to the damaged joint site.

Variations can be made in the structure of the implant carrier portion 24F of the reciprocable member 14F. In the seventh illustrated surgical instrument 10G (FIGS. 24-25), the elongate guide member 12G may be substantially like that of the sixth illustrated surgical instrument 10F. In the seventh illustrated surgical instrument 10G, the implant carrier portion 24G differs from that of the sixth illustrated surgical instrument 10F in that the base 98G and arms 100G of the implant carrier portion 24G are discrete elements rather than integral components. In the seventh illustrated surgical instrument 10G, each arm 100G has a free proximal end 106G, a flexion portion 108G, a planar portion 110G and a clip 112G at the free distal end 102G. The arms 100G are shaped so that the free proximal end 106G is on the outside of the base 98G, the flexion portion 108G of each arm 100G fits through a slot 114G in the base 98G, and the planar portion 110G and distal end portion 102G are distal to the base 98G. As in the sixth illustrated surgical instrument 10F, the arms 100G may be made of a flexible, elastic material such as a shape memory alloy like Nitinol or a polymer material. The base 98G can be made of another material that does not deform as readily, such as standard surgical grade stainless steel or a polymer for example. The base 98G can be connected to the distal rod portion of the connector member 78G through any standard connection mechanism, such as a snap fit or through a mechanical connector like a screw or nut and bolt.

The arms 100G of the implant carrier 24G of the seventh illustrated surgical instrument 10G may be made so that their natural shape is that shown in FIG. 25, with the planar portions 110G and free distal ends 102G extending radially outward and with the free proximal ends 106G extending in a generally longitudinal direction. The position and natural shape illustrated in FIG. 25 define the extended position and shape of the implant carrier 24G. FIG. 24 illustrates the retracted position and deformed shape of the implant carrier 24G. In the deformed, retracted position, the arms 100G extend in a generally distal direction and fit within the inner diameter of the tube portion 60G of the elongate guide member 12G.

The end clip portions 112G of the arms 100G of the implant carrier 24G of the seventh illustrated surgical instrument 10G are provided for temporary mounting of the orthopaedic implant 16 to the implant carrier 24G. The end clip portions 112G may be integral or discrete spring action clips that bear against portions of the implant to secure a part of the implant to each arm as illustrated in FIGS. 24-25. Portions of the implant can be received between the end clip portion 112G and the underlying planar portion 110G of the arms 100G.

The remainder of the seventh illustrated surgical instrument may be the same as that described above for the sixth illustrated surgical instrument 10F. It should however be understood that some of the features of the sixth illustrated surgical instrument 10F are optional ones; for example, the spring 82F need not be used.

Use of the seventh illustrated surgical instrument 10G would be substantially the same as that described above for the sixth illustrated surgical instrument 10F. The main distinction in use of the seventh illustrated surgical instrument would be in the manner of temporarily securing the orthopaedic implant to the implant carrier 24G. With the seventh illustrated surgical instrument 10G, part of the implant would be tucked beneath each clip portion 112G of the implant carrier 24G.

An eighth embodiment of a surgical instrument in accordance with the present invention is illustrated in FIGS. 26-30 at 10H. The eighth illustrated surgical instrument shares many common features with the sixth and seventh illustrated instruments 10F, 10G as described above. The implant carrier 24H of the eighth illustrated instrument 10H has arms 100H with end clips 112H like those of the seventh instrument 10G. The implant carrier portion 24H and the distal rod 94H of the connector member 78H of the eighth illustrated surgical instrument 10H are somewhat different from those of the sixth and seventh illustrated surgical instruments 10F, 10G. In the eighth illustrated surgical instrument 10H, the distal end of the distal rod 94H has flat parallel surfaces 120H. The base 98H of the implant carrier 24H is integral with the arms 100H, and comprises a pair of spaced parallel tabs 122H (see FIGS. 27 and 30) that are placed against the flat parallel surfaces 120H (see FIGS. 27 and 30) of the distal rod 94H. The spaced parallel tabs 122H are connected to the distal rod 94H through screws, bolts, pins or the like extending through aligned holes in the tabs 122H and flat surfaces 120H.

Use of the eighth illustrated surgical instrument 10H is like that described above for use of the sixth and seventh illustrated surgical instruments 10F, 10G.

Although the invention has been described with reference to the delivery of an orthopaedic implant to a damaged joint site, it will be appreciated that the invention has broader applications. For example, the instrument of the present invention can also be used to deliver other types of implants to other damaged tissue sites in the body. The present invention could be used to deliver any type of tissue scaffold, patch or graft to any type of tissue site, and the illustrated embodiments may be modified if desired to allow for such use. Unless otherwise expressly limited, the claims should not be construed as being limited to the delivery of orthopaedic implants to damaged joint sites.

Alternative instruments for delivering an implant to a damaged tissue site are disclosed in the following U.S. Patent Applications, filed concurrently herewith and incorporated by reference herein in their entireties: U.S. patent application Ser. No. 10/610,287 entitled "Slide and Kit for Delivering Implants," filed concurrently herewith by Thomas S. Camino, Anthony D. Zannis, John W. Kemppainen and Herbert E. Schwartz, and U.S. Provisional Pat. App. Ser. No. 60/483,805 (now U.S. application Ser. No. 10/742,202) entitled "Instrument for Delivery of Implant," filed concurrently herewith by Anthony D. Zannis, John W. Kemppainen, Andrew M.

Jacobs, Carolyn K. Day, Rhonda B. Clarke, Herbert E. Schwartz, Prasanna Malaviya and Danny E. McAdams.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

We claim:

1. A tissue repair system comprising a surgical instrument and an implant, the surgical instrument for delivering the implant to a damaged tissue site in a human body, the instrument comprising:
    an implant carrier;
    an elongate guide member having a proximal end and a distal end, the elongate guide member providing a path of travel for the implant carrier from the proximal end to the distal end;
    the implant carrier having an extended position beyond the distal end of the elongate guide member and a retracted position between the proximal and distal ends of the elongate guide member; and
    the instrument further including a reciprocable member for moving the implant carrier between the retracted and extended positions, the reciprocable member having a proximal end and a distal end, the instrument including a substantially spherical head at the distal end;
    the implant carrier mounted on the spherical head at the distal end of the reciprocable member, the implant carrier comprising a base and a plurality of arms extending outwardly from and connected to the base, the base having an interior surface shaped to complement at least a part of the substantially spherical head at the distal end of the reciprocable member, each arm having a free end opposite the base;
    the arms of the implant carrier having a general longitudinal orientation with the free ends of the arms positioned distally away from the base and the reciprocable member when the implant carrier is in the retracted position;
    the arms of the implant carrier having a general radial orientation with the free ends of the arms positioned radially away from the base and the reciprocable member when the implant carrier is in the extended position;
    the implant carrier having a transverse dimension perpendicular to the path of travel of the implant, the maximum transverse dimension of the implant carrier in the retracted position being less than the maximum transverse dimension of the implant carrier in the extended position;
    wherein the implant includes a sheet discrete from the implant carrier and attached to the free ends of a plurality of the arms of the implant carrier when the implant carrier is in the retracted position and when the implant carrier is in the extended position;
    wherein the implant has a first shape when the implant carrier is in the retracted position and a second shape when the implant carrier is in the extended position.

2. The system of claim 1 wherein the implant comprises an orthopaedic implant and the damaged tissue site comprises a damaged joint site.

3. The system of claim 1 wherein: the implant has a length, width and thickness; the elongate guide member has an inner transverse dimension between the proximal and distal ends; and at least one of the dimensions of the implant is greater than the maximum inner transverse dimension of the elongate guide member.

4. The system of claim 1 wherein the arms of the implant carrier include holes, the system further comprising suture extending through the implant and the holes of the implant carrier to temporarily secure the implant to the arms.

5. The system of claim 1 wherein the elongate guide member comprises a hollow tube and wherein at least a part of the reciprocable member is received within the hollow tube.

6. The system of claim 1 wherein the implant carrier has a retracted shape when in the retracted position and an extended shape when in the extended position, and wherein the retracted shape is different from the extended shape.

7. The system of claim 1 wherein the elongate guide member comprises a channel having an inner transverse dimension and an outer transverse dimension.

8. The system of claim 7 wherein the implant carrier has a transverse dimension perpendicular to the path of travel of the implant carrier, and wherein the maximum transverse dimension of the implant carrier in the retracted position is less than the maximum transverse dimension of the implant carrier in the extended position.

9. The system of claim 8 wherein the maximum transverse dimension of the implant carrier in the extended position is greater than the inner transverse dimension of the elongate guide member.

10. The system of claim 1 wherein the implant carrier has a transverse dimension perpendicular to the path of travel of the implant carrier, and wherein the maximum transverse dimension of the implant carrier in the retracted position is less than the maximum transverse dimension of the implant carrier in the extended position.

11. The system of claim 10 wherein the implant carrier comprises a plurality of arms, each arm having one orientation when the implant carrier is in the retracted position and having a different orientation when the implant carrier is in the extended position.

12. The system of claim 11 wherein the arms have a generally radial orientation when the implant carrier is in the extended position.

13. The system of claim 10 wherein the arms have a generally longitudinal orientation when the implant carrier is in the retracted position.

14. The system of claim 1 wherein the implant carrier and the reciprocable member are connected to define an assembly.

15. The system of claim 1 wherein the implant carrier has a shape memory that urges the implant carrier to the extended shape.

16. The system of claim 1 wherein the implant carrier is made of an elastic material.

17. The system of claim 1 wherein the reciprocable member comprises an assembly including: an elongate cylindrical shaft and a connector member connected to the elongate cylindrical shaft, the substantially spherical head being part of the connector member.

18. A surgical instrument for delivering an implant to a damaged tissue site in a human body, the instrument comprising:
    an implant carrier comprising a base and a plurality of arms extending outwardly from and connected to the base, the base having an inner surface and an outer surface;
    an elongate guide member having a proximal end and a distal end, the elongate guide member providing a path of travel for the implant carrier from the proximal end to the distal end;

the implant carrier having an extended position beyond the distal end of the elongate guide member and a retracted position between the proximal and distal ends of the elongate guide member;

the instrument further including a reciprocable member for moving the implant carrier between the retracted and extended positions, the reciprocable member having a distal end;

a substantially spherical head at the distal end of the reciprocable member;

the inner surface of the base of the implant carrier being shaped to complement at least a part of the substantially spherical head at the distal end of the reciprocable member;

the base of the implant carrier being mounted on the substantially spherical head at the distal end of the reciprocable member.

19. The instrument of claim 18 wherein the reciprocable member comprises an assembly including an elongate cylindrical shaft and a connector member connected to the elongate cylindrical shaft, the substantially spherical head being part of the connector member.

20. The surgical instrument of claim 18 in combination with an implant.

21. The combination of the surgical instrument and implant of claim 20 wherein the implant comprises an orthopaedic implant and the damaged tissue site comprises a damaged joint site.

22. The combination of the surgical instrument and implant of claim 21 wherein:
   the implant has a length, width and thickness;
   the elongate guide member has an inner transverse dimension between the proximal and distal ends; and
   at least one of the dimensions of the implant is greater than the maximum inner transverse dimension of the elongate guide member.

23. The surgical instrument of claim 18 wherein the elongate guide member comprises a hollow tube and wherein at least a part of the reciprocable member is received within the hollow tube.

24. The surgical instrument of claim 18 wherein the arms of the implant carrier have a retracted shape when in the retracted position and an extended shape when in the extended position, and wherein the retracted shape is different from the extended shape.

25. The surgical instrument of claim 18 wherein the elongate guide member comprises a channel having an inner transverse dimension and an outer transverse dimension.

26. The surgical instrument of claim 25 wherein the arms of the implant carrier have a transverse dimension perpendicular to the path of travel of the implant carrier, and wherein the maximum transverse dimension of the arms of the implant carrier in the retracted position is less than the maximum transverse dimension of the arms of the implant carrier in the extended position.

27. The surgical instrument of claim 26 wherein the maximum transverse dimension of the arms of the implant carrier in the extended position is greater than the inner transverse dimension of the elongate guide member.

28. The surgical instrument of claim 18 wherein the arms of the implant carrier have a transverse dimension perpendicular to the path of travel of the implant carrier, and wherein the maximum transverse dimension of the arms of the implant carrier in the retracted position is less than the maximum transverse dimension of the arms of the implant carrier in the extended position.

29. The surgical instrument of claim 28 wherein each arm of the implant carrier has one orientation when in the retracted position and having a different orientation when in the extended position.

30. The surgical instrument of claim 29 wherein the arms have a generally radial orientation when the implant carrier is in the extended position.

31. The surgical instrument of claim 30 wherein the arms have a generally longitudinal orientation when the implant carrier is in the retracted position.

* * * * *